(12) United States Patent
Hoffman et al.

(10) Patent No.: US 8,318,816 B2
(45) Date of Patent: Nov. 27, 2012

(54) ENHANCED TRANSPORT USING MEMBRANE DISRUPTIVE AGENTS

(75) Inventors: Allan S. Hoffman, Seattle, WA (US);
Patrick S. Stayton, Seattle, WA (US);
Niren Murthy, Atlanta, GA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/771,850

(22) Filed: Apr. 30, 2010

(65) Prior Publication Data
US 2010/0210504 A1 Aug. 19, 2010

Related U.S. Application Data

(62) Division of application No. 09/755,701, filed on Jan. 5, 2001, now Pat. No. 7,737,108.

(60) Provisional application No. 60/174,893, filed on Jan. 7, 2000.

(51) Int. Cl.
| | | |
|---|---|---|
| A61K 38/00 | (2006.01) | |
| A61K 47/00 | (2006.01) | |
| A61K 31/105 | (2006.01) | |
| A61K 31/075 | (2006.01) | |

(52) U.S. Cl. ......... 514/738; 514/1.2; 514/335; 514/707; 514/716

(58) Field of Classification Search .................... 514/1.2, 514/738
See application file for complete search history.

(56) References Cited

U.S. PATENT DOCUMENTS

| | | | |
|---|---|---|---|
| 4,571,400 | A | 2/1986 | Arnold |
| 4,657,543 | A | 4/1987 | Langer |
| 5,078,994 | A | 1/1992 | Nair |
| 5,258,453 | A | 11/1993 | Kopecek |
| 5,362,308 | A | 11/1994 | Chien |
| 5,451,411 | A | 9/1995 | Gombotz |
| 5,501,584 | A | 3/1996 | Yamamoto |
| 5,521,291 | A | 5/1996 | Curiel |
| 5,547,932 | A | 8/1996 | Curiel |
| 5,599,908 | A | 2/1997 | Raso |
| 5,603,931 | A | 2/1997 | Raso |
| 5,609,590 | A | 3/1997 | Herbig |
| 5,656,609 | A | 8/1997 | Wu |
| 5,753,263 | A | 5/1998 | Lishko |
| 5,770,627 | A | 6/1998 | Inoue |
| 5,807,306 | A | 9/1998 | Shapland |
| 5,939,453 | A | 8/1999 | Heller |
| 5,998,588 | A | 12/1999 | Hoffman |
| 6,165,509 | A | 12/2000 | Hoffman |
| 6,210,717 | B1 | 4/2001 | Choi |
| 6,358,490 | B2 | 3/2002 | Theodore |
| 6,486,213 | B1 | 11/2002 | Chen |

FOREIGN PATENT DOCUMENTS

| | | |
|---|---|---|
| WO | 96/40958 A1 | 12/1996 |
| WO | 97/04832 A1 | 2/1997 |
| WO | 97/09068 A2 | 3/1997 |
| WO | 98/33520 A1 | 8/1998 |

OTHER PUBLICATIONS

Abelev, G.I., "Alpha-Fetoprotein in Ontogenesis and Its Association With Malignant Tumors," in G. Klein et al. (eds.), ,"Advances in Cancer Research," Academic Press, Inc., New York, 1971, vol. 14, pp. 295-358.
Anderson, D.C., et al., "Enhanced In Vitro Tumor Cell Retention and Internalization of Antibody Derivatized With Synthetic Peptides," Bioconjugate Chemistry 4(1):10-18, Jan. 1993.
Baroni, S., et al., "Effect of Ibuprofen and Warfarin on the Allosteric Properties of Haem-Human Serum Albumin. A Spectroscopic Study," European Journal of Biochemistry 268(23):6214-6220, Dec. 2001.
Buschle, M., et al., "Receptor-Mediated Gene Transfer Into Human T Lymphocytes Via Binding of DNA/CD3 Antibody Particles to the CD3 T Cell Receptor Complex," Human Gene Therapy 6(6):753-761, Jun. 1995.
Cheung, C.Y., et al., "A pH-Sensitive Polymer That Enhances Cationic Lipid-Mediated Gene Transfer," Bioconjugate Chemistry 12(6):906-910, Oct. 2001.
Choi, Y.H., et al., "Lactose-Poly(Ethylene Glycol)-Grafted Poly-L-Lysine as Hepatoma Cell-Targeted Gene Carrier," Bioconjugate Chemistry 9(6):708-718, Nov. 1998.
Cordes, EH., and H.G. Bull, "Mechanism and Catalysis for Hydrolysis of Acetals, Ketals, and Ortho Esters," Chemical Reviews 74(5):581-603, Oct. 1974.

(Continued)

Primary Examiner — Jeffrey S. Lundgren
Assistant Examiner — Gregg Polansky
(74) Attorney, Agent, or Firm — Christensen O'Connor Johnson Kindness PLLC

(57) ABSTRACT

Compositions and methods for transport or release of therapeutic and diagnostic agents or metabolites or other analytes from cells, compartments within cells, or through cell layers or barriers are described. The compositions include a membrane barrier transport enhancing agent and are usually administered in combination with an enhancer and/or exposure to stimuli to effect disruption or altered permeability, transport or release. In a preferred embodiment, the compositions include compounds which disrupt endosomal membranes in response to the low pH in the endosomes but which are relatively inactive toward cell membranes (at physiologic pH, but can become active toward cell membranes if the environment is acidified below ca. pH 6.8), coupled directly or indirectly to a therapeutic or diagnostic agent. Other disruptive agents can also be used, responsive to stimuli and/or enhancers other than pH, such as light, electrical stimuli, electromagnetic stimuli, ultrasound, temperature, or combinations thereof. The compounds can be coupled by ionic, covalent or H bonds to an agent to be delivered or to a ligand which forms a complex with the agent to be delivered. Agents to be delivered can be therapeutic and/or diagnostic agents. Treatments which enhance delivery such as ultrasound, iontophoresis, and/or electrophereis can also be used with the disrupting agents.

33 Claims, 7 Drawing Sheets

OTHER PUBLICATIONS

Davaran, S., and A.A. Entezami, "Hydrophilic Copolymers Prepared From Acrylic Type Derivatives of Ibuprofen Containing Hydrolyzable Thioester Bond," European Polymer Journal 34(2):187-192, 1998.

Ding, Z., et al., "Synthesis and Purification of Thermally Sensitive Oligomer-Enzyme Conjugates of Poly(N-Isopropylacrylamide)-Trypsin," Bioconjugate Chemistry 7(1):121-125, Jan. 1996.

Feijen, J., et al., "Thermosensitive Polymers and Hydrogels Based on N-Isoproprylacrylamide," 11th European Conference on Biomaterials, Pisa, Italy, Sep. 10-14, 1964, pp. 256-260.

Fife, T.H., and L.K. Jao, "Substituent Effects in Acetal Hydrolysis," Journal of Organic Chemistry 30(5):1492-1495, May 1965.

Geisow, M.J., "Fluorescein Conjugates as Indicators of Subcellular pH: A Critical Evaluation," Experimental Cell Research 150(1):29-35, Jan. 1984.

Gold, P., and S.O. Freedman, "Specific Carcinoembryonic Antigens of the Human Digestive System," Journal of Experimental Medicine 122(3):467-481, Sep. 1965.

Guy, R.H., "Current Status and Future Prospects of Transdermal Drug Delivery," Pharmaceutical Research 13(12):1765-1769, Dec. 1996.

Haensler, J. and F.C. Szoka, Jr., "Polyamidoamine Cascade Polymers Mediate Efficient Transfection of Cells in Culture," Bioconjugate Chemistry 4(5):372-379, Sep. 1993.

Hansch, C., and W.R. Glave, "Structure-Activity Relationships in Membrane-Perturbing Agents: Hemolytic, Narcotic, and Antibacterial Compounds," Molecular Pharmacology 7(3):337-354, May 1971.

Hughes, J.A., et al., "Evaluation of Adjuvants That Enhance the Effectiveness of Antisense Oligodeoxynucleotides," Pharmaceutical Research 13(3):404-410, Mar. 1996.

Ito, Y., et al., "Control of Water Permeation by pH and Ionic Strength Through a Porous Membrane Having Poly(Carboxylic Acid) Surface-Grafted," Macromolecules 25(26):7313-7316, Dec. 1992.

Kircheis, R., et al., "Coupling of Cell-Binding Ligands to Polyethyleneimine for Targeted Gene Delivery," Gene Therapy 4(5):409-418, May 1997.

Kost, J. and R. Langer, "Responsive Polymer Systems for Controlled Delivery of Therapeutics," Trends in Biotechnology 10(4):127-131, Apr. 1, 1992.

Kratz, F., et al., "Drug-Polymer Conjugates Containing Acid-Cleavable Bonds," Critical Reviews™ in Therapeutic Drug Carrier Systems 16(3):245-288, 1999.

Kyriakides, T.R., et al., "pH-Sensitive Polymers That Enhance Intracellular Drug Delivery In Vivo," Journal of Controlled Release 78(1-3):295-303, Jan. 2002.

Linhardt, J.G., and D.A. Tirrell, "pH-Induced Fusion and Lysis of Phosphatidylcholine Vesicles by the Hydrophobic Polyelectrolyte Poly(2-Ethylacrylic Acid)," Langmuir 16(1):122-127, 2000.

Murthy, N., et al., "The Design and Synthesis of Polymers for Eukaryotic Membrane Disruption," Journal of Controlled Release 61(1-2):137-143, Aug. 1999.

Pawlak, M., et al., "Template-Assembled Melittin: Structural and Functional Characterization of a Designed, Synthetic Channel-Forming Protein," Protein Science 3(10):1788-1805, Oct. 1994.

Perales, J.C., et al., "An Evaluation of Receptor-Mediated Gene Transfer Using Synthetic DNA-Ligand Complexes," European Journal of Biochemistry 226(2):255-266, Dec. 1994.

Plank, C., et al., "The Influence of Endosome-Disruptive Peptides on Gene Transfer Using Synthetic Virus-Like Gene Transfer Systems," Journal of Biological Chemistry 269(17):12918-12924, Apr. 1994.

Prausnitz, M.R., "Reversible Skin Permeabilization for Transdermal Delivery of Macromolecules," Critical Reviews™ in Therapeutic Drug Carrier Systems 14(4):455-483, 1997.

Prausnitz, M.R., et al., "Electroporation of Mammalian Skin: A Mechanism to Enhance Transdermal Drug Delivery," Proceedings of the National Academy of Sciences USA [PNAS] 90(22):10504-10508, Nov. 1993.

Prausnitz, M.R., et al., "Transdermal Delivery of Heparin by Skin Electroporation," Nature Biotechnology 13(11):1205-1209, Nov. 1995.

Press, O.W., et al., "Endocytosis and Degradation of Murine Anti-Human CD3 Monoclonal Antibodies by Normal and Malignant T-Lymphocytes," Cancer Research 48(8):2249-2257, Apr. 1988.

Ross, G., et al., "Gene Therapy in the United States: A Five-Year Status Report," Human Gene Therapy 7(14):1781-1790, Sep. 1996.

Schroeder, U.K.O., and D.A. Tirrell, "Structural Reorganization of Phosphatidylcholine Vesicle Membranes by Poly(2-Ethylacrylic Acid): Influence of the Molecular Weight of the Polymer," Macromolecules 22(2):765-769, Feb. 1989.

Thomas, J.L., and D.A. Tirrell, "Polyelectrolyte-Sensitized Phospholipid Vesicles," Accounts of Chemical Research 25(8):336-342, Aug. 1992.

Thomas, J.L., et al., "Membrane Solubilization by a Hydrophobic Polyelectrolyte: Surface Activity and Membrane Binding," Biophysical Journal 67(3):1101-1106, Sep. 1994.

Tolstikov, V.V., et al., "Influence of Endosome-Destabilizing Peptides on Efficacy of Anti-HIV Immunotoxins," Bioconjugate Chemistry 8(1):38-43, Jan. 1997.

Tycko, B., et al., "Rapid Acidification of Endocytic Vesicles Containing Asialoglycoprotein in Cells of a Human Hepatoma Line," Journal of Cell Biology 97(6):1762-1776, Dec. 1983.

Vinogradov, S.V., et al., "Self-Assembly of Polyamine-Poly(Ethylene Glycol) Copolymers With Phosphorothioate Oligonucleotides," Bioconjugate Chemistry 9(6):805-812, Nov.-Dec. 1998.

Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.

Weaver, J.C., "Electroporation: A General Phenomenon for Manipulating Cells and Tissues," Journal of Cellular Biochemistry 51(4):426-435, Apr. 1993.

Wilder, R.B., et al., "Radioimmunotherapy: Recent Results and Future Directions," Journal of Clinical Oncology 14(4):1383-1400, Apr. 1996.

Experimental Conditions
(1) 2% RBCs in 1ml PBS buffer
(2) Incubation temperature 37C
(3) Incubation time 20 minutes
(4) Experiments done in triplicate STD < 2%

Encrypted Polymer E1: X = Y = Methoxy
Encrypted Polymer E2: X = Fluorescein, Y = Lactose
Encrypted Polymer E3: X = Hexalysine, Y = Lactose ENCRYPTED POLYMER E1 : X = y = METHOXY
ENCRYPTED POLYMER E2 : X = FLUORESCEIN, y = LACTOSE
ENCRYPTED POLYMER E3 : X = HEXALYSINE, y = LACTOSE

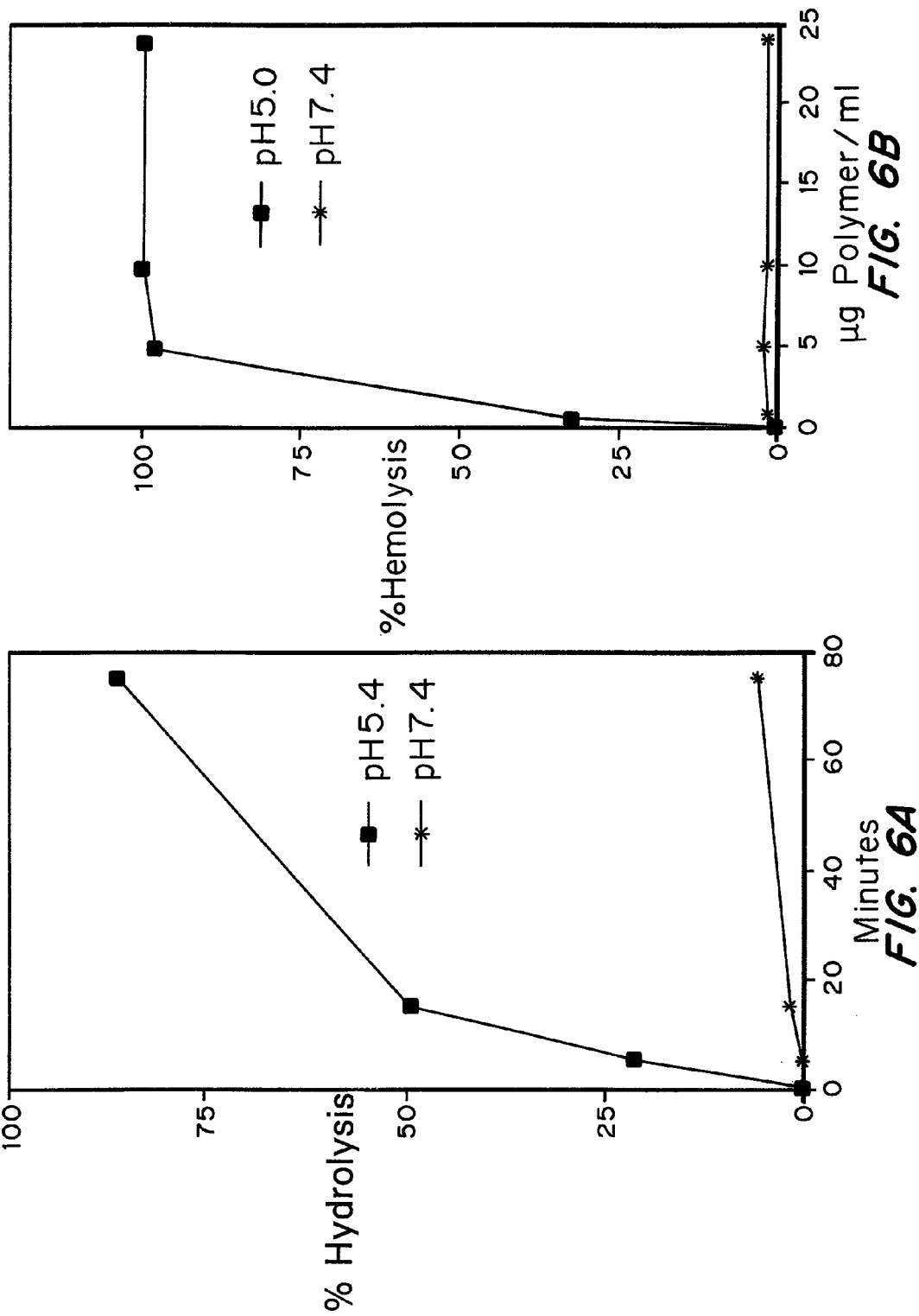

ENHANCED TRANSPORT USING MEMBRANE DISRUPTIVE AGENTS

CROSS-REFERENCES TO RELATED APPLICATIONS

This application is a divisional of U.S. patent application Ser. No. 09/755,701, filed Jan. 5, 2001 (now U.S. Pat. No. 7,737,108), which claims the benefit of U.S. Provisional No. 60/174,893, filed Jan. 7, 2000. Each application is expressly incorporated herein by reference in its entirety.

This application claims priority to U.S. Ser. No. 60/174,893 filed Jan. 7, 2000.

STATEMENT REGARDING FEDERALLY FUNDED RESEARCH

The U.S. government has certain rights in this invention by virtue of a National Institutes of Health grant, National Institutes General Medical Sciences grant GM 53771-02, 03 to 05.

The present invention is in the field of two uses of acid-sensitive polymers: (1) intracellular release of agents from inside endosomes into the cytosol, and (2) lysis of cells and microorganisms from outside, for subsequent separation, recovery, and/or analysis of their contents. In the first use, the polymer is combined with other components such as therapeutic or diagnostic agents, targeting ligands, masking molecules. In the second use, the polymer is used as a free polymer, but may be combined with chemical or physical agents used to separate, recover, identify, assay, and/or label specific intracellular components.

BACKGROUND OF THE INVENTION

Specific, efficient delivery of therapeutic and diagnostic compounds to cells, especially to the cytosol, is a major goal of many pharmaceutical companies. A number of different approaches have been utilized to increase specificity and uptake. The most common has been to target the therapeutic or diagnostic agent to specific types of cells by conjugation of the agents to antibodies that recognize antigens specifically or predominantly associated with the cells. Other agents, such as polycationic complexes, liposomes, and lipid complexes, have been employed to increase uptake of compounds generally by cells.

There are several therapeutic agents which are only effective if they are delivered intracellularly, including genetic material and various proteins. Gene therapy requires the intracellular delivery of genetic material to treat genetic disorders and other disorders which arise from dysregulation of protein expression, such as cancer. Examples of proteins include toxins, which are only poisonous once they have been released from the endosome into the cytoplasm. To increase their specificity, immunotoxins have been prepared that include the toxin conjugated to an antibody that targets tumor-associated antigens. Immunotoxins have had limited success as therapeutics, however, in part due to the inadequacy of penetration into tumor nodules and ineffective delivery of the toxin into cytosolic ribosomes.

It is often difficult to deliver compounds, such as proteins, genetic material, and other drugs and diagnostic compounds, intracellularly because cell membranes resist the passage of these compounds. Various methods have been developed to administer agents intracellularly. For example, genetic material has been administered into cells in vivo, in vitro and ex vivo using viral vectors, DNA/lipid complexes (i.e. "lipoplexes") and liposomes. DNA has also been delivered by synthetic cationic polymers and copolymers and natural cationic carriers such as chitosan. Sometimes the synthetic polymers are hydrophobically modified to enhance endocytosis. While viral vectors are efficient, questions remain regarding the safety of a live vector and the development of an immune response following repeated administration. Lipoplexes, liposomes, polycation complexes (i.e. "polyplexes") appear less effective at transfecting DNA into the nucleus of the cell.

Receptor mediated endocytosis (RME) offers an alternative means to target specific cell types and to deliver therapeutic agents intracellularly. Receptor-mediated endocytosis occurs when ligands bind to cell surface receptors on eukaryotic cell membranes, initiating or accompanying a cascade of nonequilibrium phenomena culminating in the cellular invagination of membrane complexes within clathrin-coated vesicles. Compounds which interact with specific cell surface receptors are employed to target specific cell surface receptors. These compounds are endocytosed into the endosomes once they interact with the cell surface receptors. Linkages of the cell ligands have been made directly with these compounds, or, in the case of DNA, through conjugation with polycationic polymers such as polylysine, polyethyleneimine, and DEAE-dextran which are then complexed with the DNA. Haensler et al., *Bioconj. Chem.*, 4:372-379 (1993).

Even after therapeutic agents are delivered intracellularly, normal trafficking in the cell can minimize their effectiveness. For example, certain antibody-antigen conjugates are readily endocytosed. However, after endocytosis, the antibody is not released into the cytosol but rather remains isolated in endosomes until it is trafficked to a lysosome for degradation. Press, O. W. et al., *Cancer Research*, 48: 2249-2257 (1988). Endosomes are membrane bound phospholipid vesicles which function in intracellular trafficking and degradation of internalized proteins. The internal pH of the endosomes is between 5.0 and 6.5. A toxin conjugated with this antibody will be similarly isolated in the endosome, and, if trafficked to a lysosome, will be rendered ineffective. Genetic material, being negatively charged, is often complexed with polycationic materials, such as cationic lipids, chitosan, polyethyleneimine and polylysine, for delivery to a cell. Both immunotherapy and gene therapy using polycation/nucleic acid complexes are also limited by trafficking of the complexes by the cell from endosomes to lysosomes, where the antibody conjugates or nucleic acids are degraded and rendered ineffective.

Accordingly, a major limitation of many potentially useful therapies is that the agents, even if they can be targeted to the desired cells and endocytosed by the cells, often are not effectively released from endosomes into the cytosol, but are degraded by lysosomes.

Several methods have been proposed to avoid or minimize lysosomal degradation of these agents. One method involves including lysosomotrophic agents such as chloroquine in formulations used to administer therapeutic agents intracellularly. Another method involves disrupting the endosome so that the agent is delivered into the cytosol before it is transported to and degraded by the lysosomes. It is preferable to disrupt the endosome so that the material never comes in contact with the lysosomes. At least two pathways have been developed for disrupting the endosomal membrane. One method takes advantage of the pH inside the endosomes, and uses materials which are relatively hydrophilic at physiological pH (around 7.4) and relatively hydrophobic at the pH inside of the endosomes. Examples of such materials are carboxylic acid containing polymers such as the hydrophobic polyacid poly(2-ethylacrylic acid) (PEAA), which are negatively charged at physiologic or alkaline pH and uncharged at the pH inside the endosome due to protonation of the carboxylic acid moieties.

PEAA has been shown to disrupt lipid membranes in a pH dependent manner, permeabilizing and solubilizing membranes at an acidic pH (approximately 6.3), while having no effect at alkaline pH. Thomas, J. L. et al., *Biophysical Journal*, 67:1101-1106 (1994); Thomas, J. L. et al., *Acc. Chem. Res.*, 25:336-342 (1992). It has been postulated that the effects of PEAA are due to its amphipathicity rather than structure, consistent with a hydrophobically driven micellization process. A similar process has been hypothesized for the interaction of apolipoproteins, melittin, and other amphipathic α-helix based polypeptides with lipid membranes.

Various peptides also disrupt endosomal membranes in a pH dependent manner. Examples of peptides shown to disrupt liposomes, erythrocytes, and endosomes, include viral peptides, such as influenza virus peptides and peptides that include the 23 amino terminal amino acid sequence of influenza virus hemagglutinin, and related peptides with which viruses destabilize endosomal membranes in a pH dependent manner, such as GAL4 (also known as EALA), which includes repeating glutamic acid-alanine-leucine-alanine blocks. These peptides have been conjugated with DNA complexes that utilize a receptor mediated endocytosis pathway for uptake into cultured cells. A strong correlation was observed between pH specific erythrocyte disruption and gene transfer. C. Plank et al., *J. Biol. Chem.*, 17(269):12918-12924 (1994); J. A. Hughes et al., *Pharm Res.*, 13(3):404 (1996). Other peptides include melittin and derivatives, which are membrane channel formers. M. Pawlak et al., *Protein Science*, 3:1788-1805 (1994). GAL4 has been conjugated with a polycationic polymer (polyamidoamine cascade polymers, dendritic polymers synthesized from methyl acrylate and ethylenediamine), and the polycationic polymeric block has been complexed with plasmids encoding reporter genes. J. Haensler et al., *Bioconj. Chem.*, 4:372-379 (1993). These compounds are believed to disrupt the membrane by changing from a random coil to hydrophobic helix, thereby fusing with and/or forming a pore in the membrane.

None of these methods or materials have solved the transport or delivery problems. It would therefore be advantageous to provide improved compositions for delivering diagnostic and/or therapeutic agents to the cytoplasm of a cell without significant lysosomal degradation.

It is another object of the present invention to provide compositions for enhanced transport of diagnostic or therapeutic agents, including proteins and genetic material, or other molecules through other cell membranes, cell barriers or cell layers, or through lipid membranes.

It is a further object of the present invention to provide compositions for the release of cell or microorganism contents for subsequent recovery and/or analysis.

It is a further object of the present invention to provide such compositions that can be controlled and manipulated externally, for example, using non-invasive means such as ultrasound to enhance delivery or transport.

SUMMARY OF THE INVENTION

Compositions and methods for transport or release of therapeutic and diagnostic agents or metabolites or other analytes from cells, compartments within cells, through cell layers or cell barriers, or lipid membranes are described. The compositions include a membrane disruptive agent or "membrane barrier transport enhancing agent" which becomes membrane disruptive following endocytosis, releasing cellular contents or releasing a therapeutic, diagnostic or prophylactic agent to be delivered.

The membrane disruptive agent is a hydrophobic polymer (or at least is more hydrophilic than hydrophobic at a define pH, such as pH 7, as compared to a lower pH, such as pH 5), which in the preferred embodiment is designed to be stable and inert at physiologic conditions and to become both endoosomolytic and drug-releasing as the pH drops within the endosome. The membrane disruptive agent may be a hydrophobic polymer which is coupled to a hydrophilic polymer or multiple hydrophilic groups which are released after endocytosis to expose the hydrophobic polymer or a hydrophilic polymer which is protonated after endocytosis to yield a hydrophobic polymer, all of which are membrane disruptive. The hydrophilic components are preferably coupled to the hydrophobic component via a degradable linkage, most preferably an acid labile linkage which is cleaved following endocytosis. In one embodiment, the membrane disruptive agent is coupled to hydrophilic groups in an amount effective to make the polymer soluble in an aqueous solution and allow passage through the cell wall of the polymer. The hydrophilic groups are coupled to the polymeric backbone via linkages that are disrupted upon exposure to an appropriate stimulus, typically a change in pH, and most typically a decrease in pH from physiological pH (i.e., typically pH 7.4) to the pH of the endosome (approximately between 5 and 6.5). With the removal of the hydrophilic groups, the polymer again becomes hydrophobic and disrupts the endosomal membrane, releasing the endosomal contents into the cytoplasm.

The hydrophilic groups can be linked directly to the hydrophobic polymeric backbone or can be on a polymer which is linked to the hydrophobic polymer via degradable (or disruptable) linkages. In either case, exposure to low pH or the stimulus which disrupts the linkages releases the hydrophobic polymeric backbone, which then disrupts the endosomal or other cellular membrane. In a preferred embodiment, the hydrophilic groups are a polymer, such as polyethylene glycol (PEG), which helps prevent uptake and clearance of the composition by phagocytic cells of the reticuloendothelial system (RES) prior to uptake by the cells to which the therapeutic, diagnostic or prophylactic agent is to be delivered. In another embodiment, the hydrophilic groups are PEG groups, which are conjugated directly to drug molecules and are conjugated to the hydrophobic backbone by acid degradable linkages (also referred to herein as "pH-degradable linkages"). In another embodiment, the hydrophilic polymer contains disulfide-linked drugs, designed to deliver drug-SH molecules within the cytoplasm.

The membrane disruptive agents may be used to deliver "fragile" drugs, such as DNA plasmids, antisense oligodeoxynucleotides (ODNs) and cytoplasmic-based protein therapeutics, as immunotoxins. They may serve as carriers for proteins or peptides designed for entry into the MHC 1 pathway for vaccine applications. The polymeric drug carriers may also be targeted to specific cell targets. The agents to be delivered may be linked to either the hydrophilic or hydrophobic components, or to the polymer which is converted to a hydrophobic polymer after endocytosis. In the preferred embodiment these linkages are acid degradable. In a preferred embodiment, these linkages are acetal bonds. In another embodiment, the therapeutic, diagnostic or prophylactic agent is bound to acid degradable linkages by disulfide bonds. The agent to be delivered can also be coupled via polycationic materials like polylysine, polyethyleneimine, or chitosan, which form a complex with the agent to be delivered, stabilizing the agent and in some cases further enhancing endocytosis by causing membrane disruption, and/or targeting molecules which direct delivery and uptake to specific cells.

The compositions can also include a carrier, for example, nanoparticles or microparticles, liposomes or lipid vesicles. The lipid vehicles, especially cationic liposomes, may themselves cause membrane disruption. The membrane disrupting agents can be incorporated onto, into or within these carriers. They can be mixed with, ionically complexed to, or chemically conjugated to the polyplex or lipoplex carrier particles. The compositions can be applied to solid surfaces, form hydrogels, and/or act as drug carriers.

The compositions are particularly useful in a wide variety of diagnostic assays, for example, where cellular contents are to be assayed for levels of particular analytes, for genetic material, or for the presence of specific cell types, or a variety of microorganisms as contaminants, or as bacterial or parasitic infections, or where a diagnostic agent is to be delivered into the cell to be diagnosed. The compositions can be administered systemically or locally using known methodologies, in an amount effective to diagnose or treat a patient in need thereof. The materials are particularly useful for delivery of genetic material to cells in vitro, for example, for gene therapy and for delivery of drugs to cells in vivo. Delivery of the agents, or disruption of the membrane to release cell or organelle contents can also be achieved by adjusting the pH, for example, by adding acid to the environment of the cells or organelles, to trigger membrane disruption.

BRIEF DESCRIPTION OF THE DRAWINGS

FIG. 6A is a graph of the pH-dependent hydrolysis of Polymer E1. Percent hydrolysis versus time (minutes) is plotted for pH 5.4 (squares) and pH 7.4 (stars).

FIG. 6B is a graph of the pH-dependent hemolysis by Polymer E1. Percent hemolysis versus concentration of Polymer E1 (µg/ml) is plotted for pH 5.0 (squares) and pH 7.4 (stars).

DETAILED DESCRIPTION OF THE INVENTION

Figure 1:
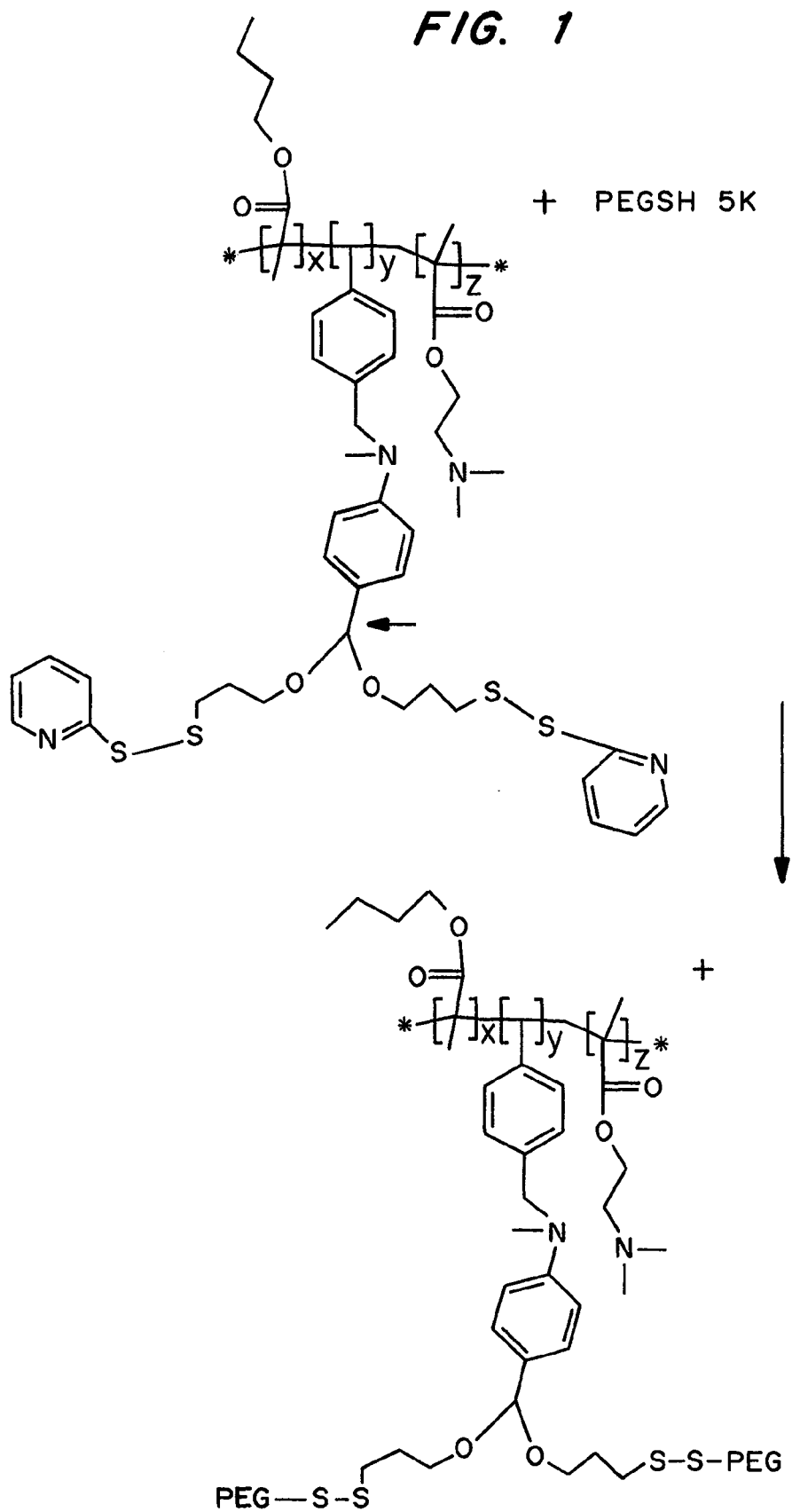
FIG. 1 is a schematic of the synthesis of a conjugate of a hydrophobic polymeric backbone having PEG (MW 5000) coupled thereto. As depicted, the hydrophobic polymer includes a hydrophobic backbone and at least one side chain which increases water solubility, and a pH unstable linker. The PEG is coupled via a acetyl bond on the pH unstable linker to the hydrophobic polymer.

A. Compositions for Enhancing Membrane Transport and Methods of Manufacture Thereof.

The compositions for enhancing membrane transport include:

I. A membrane disruptive component, typically a polymer including a) Synthetic vinyl-type cationic/hydrophobic polymers and their hydrophilic derivatives that become hydrophobic at the pH of the endosome, b) Non-vinyl or naturally-derived polymers and their hydrophilic derivatives that become hydrophobic at the pH of the endosome, c) Peptides which are membrane disruptive, such as those which mimic certain viral peptides, d) Phospholipid Bilayer Disrupting Agents, or e) Polymers which become membrane disruptive upon exposure to a stimulus other than pH.

II. Optionally, a hydrophilic component which makes the membrane disruptive component soluble and, preferably, "long circulating" in physiologic media, typically a) hydrophilic polymers like PEG, or b) groups having an appropriate charge and in an amount neutralizing the hydrophobicity of the membrane disruptive component which are coupled directly to the membrane disruptive component, and III. Acid degradable or stimulus-disruptive linkages coupling the membrane disruptive component (also referred to herein as the hydrophobic polymeric backbone) and the hydrophilic components or coupling the membrane disruptive component directly to a therapeutic, diagnostic or prophylactic agent.

IV. The conjugate is coupled to a therapeutic, diagnostic or prophylactic agent to be delivered, via covalent or ionic bonds, directly or via an indirect linkage to the hydrophilic and/or hydrophobic components. V-VI. Optionally, the conjugate may also have a targeting ligand coupled to the hydrophobic polymeric backbone or to the hydrophilic component, endosomal transport enhancing agents or lysosomal inhibitors, and/or carriers.

I. Membrane Barrier Transport Enhancing Agents

Any membrane disrupting agent can be used to alter transport through cell membranes, liposomes or other lipid vesicles, membranes within a cell or through a layer of cells such as the stratum corneum, which does not adversely affect the ability of the therapeutic, diagnostic or prophylactic agent to function following delivery, and which disrupts the membrane or interstitial spacing such that the agent to be delivered passes through the cell or cell layer(s). Although referred to herein as "membrane disruptive agents", the agents may not actually disrupt the membrane and therefore the term is used interchangeably with "membrane barrier transport enhancing agents". Although described herein with reference to disruption of endosomal membranes as compared to cell membranes, cell barriers, layers of cells, or liposomal membranes, the agents can be used for delivery to cells, out of cells, or across cell layers or barriers such as the blood brain barrier, or liposomes or other lipid vesicles by disruption of membranes other than endosomal membranes, if the stimuli to induce disruption can be selectively provided at the cell membrane to be disrupted.

Polymers that can be used to disrupt membranes have enough hydrophobic groups attached to them to cause them to partition into membranes such as endosomal membranes and disrupt them.

a) Synthetic Vinyl-Type Cationic/Hydrophobic Polymers and their Hydrophilic Derivatives that become Hydrophobic at the pH of the Endosome.

Any polymer can be used which is not hydrophobic at physiological pH, typically in the range of between 6.8 and 7.5, and approximately 7.4 inside cells, but which becomes hydrophobic at the pH inside the endosomes (between 5.0 and 6.5). Polymers which include multiple carboxylic acid groups, for example, polymers with more than 0.5 carboxylic acid groups per monomer on average, tend to be relatively hydrophilic at pH ranges in which the carboxylic acid groups are deprotonated, and tend to be relatively hydrophobic at pH ranges in which the carboxylic acid groups are protonated. The pKa for carboxylic acid groups is such that they tend to be protonated at the pH range present in the endosomes. Examples of these endosomal membrane disrupting agents include pH sensitive polymers which do not disrupt cell membranes at physiological pH but which disrupt the endosomal membrane at the pH range inside the endosomes, random, block or graft copolymers of these polymers with peptides which become hydrophobic at the pH range in the endosome and polymers, proteins and peptides which attack phospholipid bilayers.

The molecular weight of the vinyl-type polymers has marked effect on the pH dependence of permeability of the hydrophobic polymer to the bilayer membrane. For example, Tirrell et al., reported that PEAA with higher molecular weight tends to disrupt a phosphatidylcholine vesicle membrane at a relatively higher pH while PEAA with lower molecular weight tends to disrupt the phosphatidylcholine vesicle membrane at a relatively lower pH. A 50% fusion of PEAA into a phosphatidylcholine vesicle has been shown to occur at pH 6.25 for PEAA with a MWw (i.e. weight average molecular weight) of 24,900 Daltons. The same 50% fusion of PEAA has been shown to occur at pH 5.5 for PEAA with a MWw of 6,000 dalton. See J. G. Linhardt and D. A. Tirrell, "pH-Induced Fusion and Lysis of Phosphatidylcholine Vesicles by the Hydrophobic Polyelectrolyte Poly(2-ethylacrylic Acid)", *Langmuir*, 16:122-27 (2000); U. K. O, Schroeder, D. A. Tirrell, "Structural Reorganization of Phosphatidylcholine Vesicle Membranes by Poly(2-ethylacrylic acid). Influence of the Molecular Weight of the Polymer", *Macromolecules*, 22:765-69 (1989).

Random, block and graft copolymers that include acrylate groups and alkyl substituted acrylate groups are preferred. Preferably, the alkyl group is a C1-6 straight, branched or cyclic alkane. Preferred monomers for use in preparing the polymeric materials include poly(ethylacrylic acid) (PEAA), poly(propylacrylic acid) (PPAA) and poly(butylacrylic acid) (PBAA). Copolymers of these monomers by themselves or including acrylic acid can be used. An example of a random copolymer is EA-AA. This may be modified by grafting of either component to the backbone of the other component, or as a block copolymer of a block of one polymer conjugated to a block of the other.

The backbone polymer may be a synthetic, free radical polymerizing type of polymer or copolymer prepared from cationic (or basic) monomers such as: vinyl imidazole, vinyl pyridene, vinyl formamide or acetamide (polymers of which can be hydrolyzed to poly[vinyl amine]), aminoethyl or dimethylaminoethyl methacrylate (or acrylate), aminoethyl or dimethyl aminoethyl (or propyl)methacrylamide (or acrylamide), vinyl aniline and its derivatives. These monomers may be copolymerized with more hydrophobic monomers such as the alkyl acrylates or methacrylates, styrene, and others. If the hydrophobic character of this backbone polymer is too great, making it difficult to dissolve even when bound to the hydrophilic component as described in more detail below, then it can be made more hydrophilic by copolymerizing the hydrophobic monomers or polymer with a more hydrophilic monomer such as HEMA (2-hydroxyethyl methacrylate), vinyl pyrrolidone, hydroxypropyl methacrylamide (HPMA) or acrylamide.

Random, block or graft copolymers of pH sensitive polymers with sulfonate groups can also be synthesized. The sulfonate groups will interact strongly via ion-ion interactions with the charges on the cationic polymer or lipid DNA carriers and should enhance the physical coupling of the sulfonated polymer with the cationic carrier. The carboxyl groups on the pH-sensitive polymers should not interact as strongly as the sulfonate groups with the cationic groups on the carriers. The pH sensitive polymers can be modified by inclusion of AMPS, a sulfonated propyl acrylamide monomer. In addition to pendant hydrophobic and —COOH groups in the polymers, monomers that have pendant sulfonate groups can be added (e.g., using a monomer called AMPS, which is commercially available), which would permit strong ionic bonding of the membrane-disruptive polymer to a cationic DNA carrier, including cationic lipid micelles or liposomes, polymeric cations and dendrimers. The sulfonate group ($SO_3$—) will couple much more strongly to a quaternary cationic group than will the COO— group, and at the pHs of 5-6.5 within the endosome, only the carboxyl group will be protonated, due to the low pKa of the $SO_3$— group.

b) Non-vinyl or Naturally-Derived Polymers and their Hydrophilic Derivatives that become Hydrophobic at the pH of the Endosome.

A number of other non-vinyl "naturally-derived" or synthesized cationic polymers may also be used as the backbone polymer, including synthetic or natural polypeptides such as poly(L-lysine), polyarginine, protamine, chitosan, aminoethyl dextran, and polyethylene imine. These are particularly useful for complexing anionic drugs such as nucleotide molecules, including oligonucleotides such as antisense, ribozymes, and ribozyme guide sequences, as well as genes. Agents to be delivered can be complexed with the polymer or conjugated to them. The polymers such as the poly(L-lysine and arginine) can also be modified by conjugating a reactive Z-hydrophobic-X-hydrophilic group or Z-hydrophobic group to their backbones, where Z is a group that can react with or be activated to react with the amine groups in the polymer backbone, and X is a pH-degradable linkage, and then coupling the agent to be delivered to the Z-hydrophobic-X-hydrophilic conjugate via the Z group.

Other polymers such as cellulosics, hyaluronic acid, alginic acid, polysaccharides, poly HEMA, polyacrylic or methacrylic acid, poly alkylacrylic acids such as poly(propyl acrylic acid) and so on may be used as backbones for complexing or conjugating a drug along with conjugation of the reactive Z-hydrophobic-X-hydrophilic group or Z-hydrophobic group to the backbone polymer.

The polymers can also include blocks of other polymeric materials, including polycationic blocks such as polylysine and chitosan that form complexes with genetic material. Such polycationic polymers are well known to those of skill in the art. The polymers can also be covalently coupled to one or more naturally-occurring polysaccharides, e.g. a hydrocarbon ester of carboxymethyl cellulose (CMC), hydrocarbon esters or amides of hyaluronic acid (HA). The hydrocarbons can be or can include cholesterol and other hydrophobic molecules.

Important variables of polymer composition which alter polymer characteristics include molecular weight ("MW")

and its distribution, tacticity of the backbone polymer bond configurations, copolymer structure, degradable bonds, and polymer composition. For example, polymers can be synthesized in stereoregular forms (e.g., isotactic or syndiotactic forms, which are stereoregular), or atactic form, which lacks any stereoregularity. This can be controlled, for example, through selection of appropriate catalysts and solvents for the polymerization. Copolymers are formed from two or more different monomers. These can be random copolymers, with random organization of the two monomers along the backbone of the polymer chain, or they may be block copolymers, with long segments of one polymer attached to relatively long segments of the other. They can also be graft copolymers, where one of the two components is a macromonomer, or is coupled as a side chain to the other, which forms the copolymer backbone. The block or graft copolymers can contain segments that act to disrupt lipid membranes and other segments that can carry ionically or covalently coupled drugs, where DNA is an example of an ionically bound drug. The covalently coupled drugs may be coupled via acid degradable bonds.

c) Peptides

Peptides which lose their charge at a lower pH and become hydrophobic, thereby altering their structure or other properties, disrupting the endosomal membrane in the process, can be used as polymeric blocks with the pH sensitive polymers described above. Examples of such peptides include viral and bacterial peptides, such as influenza virus peptides, peptides that include the 23 amino terminal amino acid sequence of influenza virus hemagglutinin, and peptides that mimic the manner in which viruses destabilize endosomal membranes in an acidification dependent manner. Such peptides mimic the structure of virus proteins which destabilize endosomal membranes. For example, peptides based upon the influenza virus protein hemagglutinin (HA) have been shown to undergo a structural change at lower pH due to protonation of carboxyl groups, triggering formation of an a-helical conformation. These amphipathic helices can then penetrate and cause disruption of the endosomal membrane. Examples of suitable peptides include EALA and mellitin.

These peptides can be incorporated into polymers, for example, the pH sensitive polymers described above. GAL4-polyacrylic acid graft copolymers can be prepared, for example, by polymerizing an N-acryloxysuccinimide monomer via free radical polymerization, reacting the resulting poly-(N-hydroxysuccinimide) (poly-NHS) with a desired mole ratio of GAL4 in a polar aprotic solvent such as dimethylsulfoxide (DMSO), and hydrolyzing the remaining unreacted NHS groups to yield the graft co-polymer. The mole ratio of GAL4 to the acryloxy monomers should be less than one, such that carboxylic acid groups are present in the final polymer. Without the remaining carboxylic acid groups, the ability of the polymer to respond to changes in pH is limited. The incorporation of peptides into these polymers dramatically enhances and in some cases can confer activity on the peptides when they are otherwise ineffective.

Structurally related graft co-polymers can be prepared by substituting different NHS-substituted monomers, for example, methyl acryloxy succinimide, ethyl acryloxy succinimide, propyl acryloxy succinimide, butyl acryloxy succinimide, and combinations thereof.

Block copolymers can be prepared by synthesizing sequences of EALA attached to sequences of mellitin. Block copolymers can also be prepared that include different synthetic polymers using group transfer polymerization techniques. Conjugates of two different polymers or peptides may be more effective than either one alone, or physical mixtures of the two. Purification of the conjugate from the free components can be performed using ion exchange chromatography, for example, strong cation exchange. It is advantageous to remove the free polymer from the conjugate of the polymer and the agent to be delivered. The free polymer, being negatively charged, can be separated from the conjugate via ion exchange chromatography. The negative charge serves to alter the affinity of the antibody for the cation exchange matrix, making it possible to separate free antibody from the conjugate as well.

d) Phospholipid Bilayer Disrupting Agents

Polypeptides and polymers which include imidazole groups can also be endosomal membrane disrupting agents, which function by attacking the phospholipid bilayer at a lower pH. The imidazole groups hydrolyze phosphate esters and carboxyl esters. Hydrolysis of lipids leads to the formation of lysophospholipids and fatty acids, both of which destabilize phospholipid bilayers and cause the disruption of cell membranes. Accordingly, these polymers and peptides can be used as polymeric blocks and coupled to the pH sensitive polymers and proteins described above.

Suitable polymers and polypeptides include polymers including vinyl imidazole monomeric units and proteins and peptides containing histidine residues. For example, monomeric ethyl acrylic acid can be copolymerized with vinyl imidazole. At pH 7.4, this polymer will not interact with the lipid bilayer; however, at low pH this polymer will become hydrophobic and interact with the endosomal membrane, bringing the imidazole group close to the phospholipids, where it can hydrolyse them and cause membrane disruption. Polyimidazole has its greatest catalytic activity when it is half protonated and half deprotonated. The pKa of polyimidazole is about 6.5, and hence polyimidazole should have greater activity in endosomes. These polymers and polypeptides can be used to form block or graft copolymers with the pH sensitive polymers and peptides described above.

e) Polymers which Become Membrane Disruptive Upon Exposure to a Stimulus Other than pH.

Materials which become membrane disruptive agents in response to stimuli other than pH, including temperature, light, electrical stimuli, radiation, ultrasound, and combinations thereof, alone or in further combination with pH sensitive agents, can also be used. Illustrative polymers described herein are temperature, pH, ion, and/or light-sensitive polymers. A. S. Hoffman, *Artif. Organs,* 19:458-467 (1995); G. H. Chen & A. S. Hoffman, *Macromol. Chem. Phys.,* 196:1251-1259 (1995); M. Irie & D. Kungwatchakun, Maokromol. Chem., *Rapid Commun.,* 5:829-832 (1985); and M. Irie, *ACS Polym. Preprints,* 27(2):342-343 (1986).

Temperature Sensitive Polymers

Temperature sensitive polymers are described by Feijen, et al., 11*th European Conf. on Biomtls.,* 256-260 (1994); Monji & Hoffman, *Appl. Biochem. and Biotech.,* 14:107-120 (1987); Monji, et al., *Biochem. and Biophys. Res. Comm.,* 172:652-660 (1990); Park, et al., *J. Biomtls. Sci. Polymer Ed.,* 4:493-504 (1993); Chen and Hoffman, *Bioconj. Chem.,* 4:509-514 (1993); Ding, et al., *Bioconj. Chem.,* 7:121-125 (1995); Chen and Hoffman, *Macromol. Chem. Phys.,* 196:1251-1259 (1995); Takei, et al., *Bioconj. Chem.,* 4:42-46 (1993); Takei, et al., *Bioconj. Chem.,* 4:341-346 (1993); Takei, et al., *Bioconj. Chem.,* 5:577-582 (1994); Matsukata, et al., *J. Biochem.,* 116:682-686 (1994); Chilkoti, *Bioconj. Chem.,* 5:504-507 (1994).

Illustrative embodiments of the many different types of temperature-responsive polymers are polymers and copolymers of N-isopropyl acrylamide (NIPAAm). PolyNIPAAm (PNIPAAm) is a thermally sensitive polymer that precipitates out of water at 32_C, which is its lower critical solution temperature (LCST), or cloud point (Heskins & Guillet, *J. Macromol. Sci.-Chem.*, A2: 1441-1455 (1968)). When PNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.*, 13:2551-2570 (1975); Priest et al., ACS Symposium Series, 350:255-264 (1987); and Heskins & Guillet, *J. Macromol. Sci.-Chem.*, A2:1441-1455 (1968). Copolymers can be produced having higher or lower LCSTs and a broader temperature range of precipitation.

Temperature-responsive polymers such as PNIPAAm have been conjugated randomly to affinity molecules, such as monoclonal antibodies, for example, as described in U.S. Pat. No. 4,780,409 to Monji, et al.; and Monji & Hoffman, *Appl. Biochem. Biotechnol.*, 14:107-120 (1987). Activated PNIPAAm has also been conjugated to protein A, various enzymes, biotin, phospholipids, RGD peptide sequences, and other interactive molecules.

By randomly copolymerizing a thermally-sensitive NIPAAm with a small amount (e.g. less than 10 mole percent) of a pH-sensitive comonomer such as acrylic acid (AAc), a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature sensitive component may be "eliminated" (e.g., no phase separation seen up to and above 100_C). Graft and block copolymers of pH and temperature sensitive monomers can be synthesized which retain both pH and temperature transitions independently. G. H. Chen & A. S. Hoffman, *Nature*, 373:49-52 (1995).

Polymers Sensitive to Other Environmental Stimuli

Polymers sensitive to other environmental stimuli, such as ion concentration, ion affinity and differential solubility, are reported by Fujimura, et al., *Biotech. Bioeng.*, 29:747-752 (1987); Nguyen & Luong, *Biotech. Bioeng.*, 34:1186-1190 (1989); Taniguchi, et al., *Biotech. Bioeng.*, 34:1092-1097 (1989); Monji, et al., *J. Biomtls. Sci. Polymer Ed.*, 5:407-420 (1994); Chen & Hoffman, *Biomtls.*, 11:631-634 (1990); Stayton, et al., *Nature*, 378:472-474 (1995).

Polysaccharides such as carrageenan change their conformation, for example, from a random to an ordered conformation, as a function of exposure to specific ions such as K+ or Ca++. A solution of sodium alginate may be gelled by exposure to Ca++. Other specific ion-sensitive polymers include polymers with pendant ion chelating groups, such as histidine or EDTA. A lipid or phospholipid group can also be chemically or ionically coupled to the membrane-disruptive polymer backbones, to facilitate its insertion into cationic lipid micelle or liposome DNA carrier systems. This could be done, for example, by conjugating a fatty alcohol to the carboxyl pendant group to form an ester group, or by conjugating a dipalmitoyl phosphatidyl ethanolamine to the carboxyl pendant group to form an amide group. Lipid groups could also be chemically-coupled to a terminal or pendant group of the polymers. If the sulfonated monomer AMPS, described above, is used in the membrane-disruptive polymer, then one could ionically-complex a cationic lipid to the polymer to facilitate its insertion into cationic lipid drug carrier systems.

Light-Sensitive Polymers

Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state. It is also possible to incorporate multiple environmental sensitivities in the same polymer, such as temperature and light sensitivity, by copolymerization.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g. temperature-) responsive polymer. A number of protocols for such dye-conjugated monomer syntheses are known.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes. Ciardelli, *Biopolymers*, 23:1423-1437 (1984); Kungwatchakun & Irie, *Makromol. Chem., Rapid Commun.*, 9:243-246 (1988); Lohmann & Petrak, *CRC Crit. Rev. Therap. Drug Carrier Systems*, 5:263 (1989); Mamada et al., *Macromolecules*, 23:1517 (1990). When this type of dye is exposed to 350-410 nm UV light, the trans form of the aromatic diazo dye, which is more hydrophobic isomer, is isomerized to the cis form, which is dipolar and more hydrophilic. This isomerization can cause the polymer to undergo conformational changes, causing a turbid polymer solution to clear, depending on the degree of dye-conjugation to the backbone and the water solubility of the main unit of the backbone. Exposure to about 750 nm visible light will reverse the phenomenon. Conversion of the pendant group from a hydrophilic to a hydrophobic state can also cause individual chains to expand or collapse their conformations. Such light-sensitive dyes may also be incorporated along the main chain of the backbone, such that the conformational changes due to light-induced isomerization of the dye will cause polymer chain conformational changes. When the polymer main chain contains light sensitive groups (e.g., azo benzene dye) the light-stimulated state may actually contract and become more hydrophilic upon light-induced isomerization.

Light can be used as a stimulus, for example, which converts a cationic dye to a neutral, more hydrophobic dye, thereby releasing anionic DNA and also producing a more hydrophobic molecule which can disrupt endosomal membranes.

II. Hydrophilic Components.

a) Hydrophilic Polymers

A wide variety of hydrophilic polymers can be used to solubilize the hydrophobic polymer component before it is exposed to the stimuli at the site where delivery of the therapeutic, diagnostic or prophylactic agent is desired. In a preferred embodiment, the hydrophilic component is a polyalkylene glycol or polyalkylene oxide, such as polyethylene glycol (PEG) or polyethylene oxide (PEO). In a preferred embodiment, the hydrophilic polymer is PEG. Previous studies have shown that PEGylation can minimize clearance through the reticuloendothelial (RES) system, significantly improving the stability, circulation lifetime, and biodistribution properties of a wide variety of delivery systems. M. C. Woodle, in *Poly(ethylene-glycol) Chemistry and Biological Applications*, J. M. Harris J M & S. Zalipsky Eds., (Washington, D.C.: American Chemical Society 1997), pp 60-77. PEGylated therapeutics have also been approved for human use by the FDA.

Figure 3:
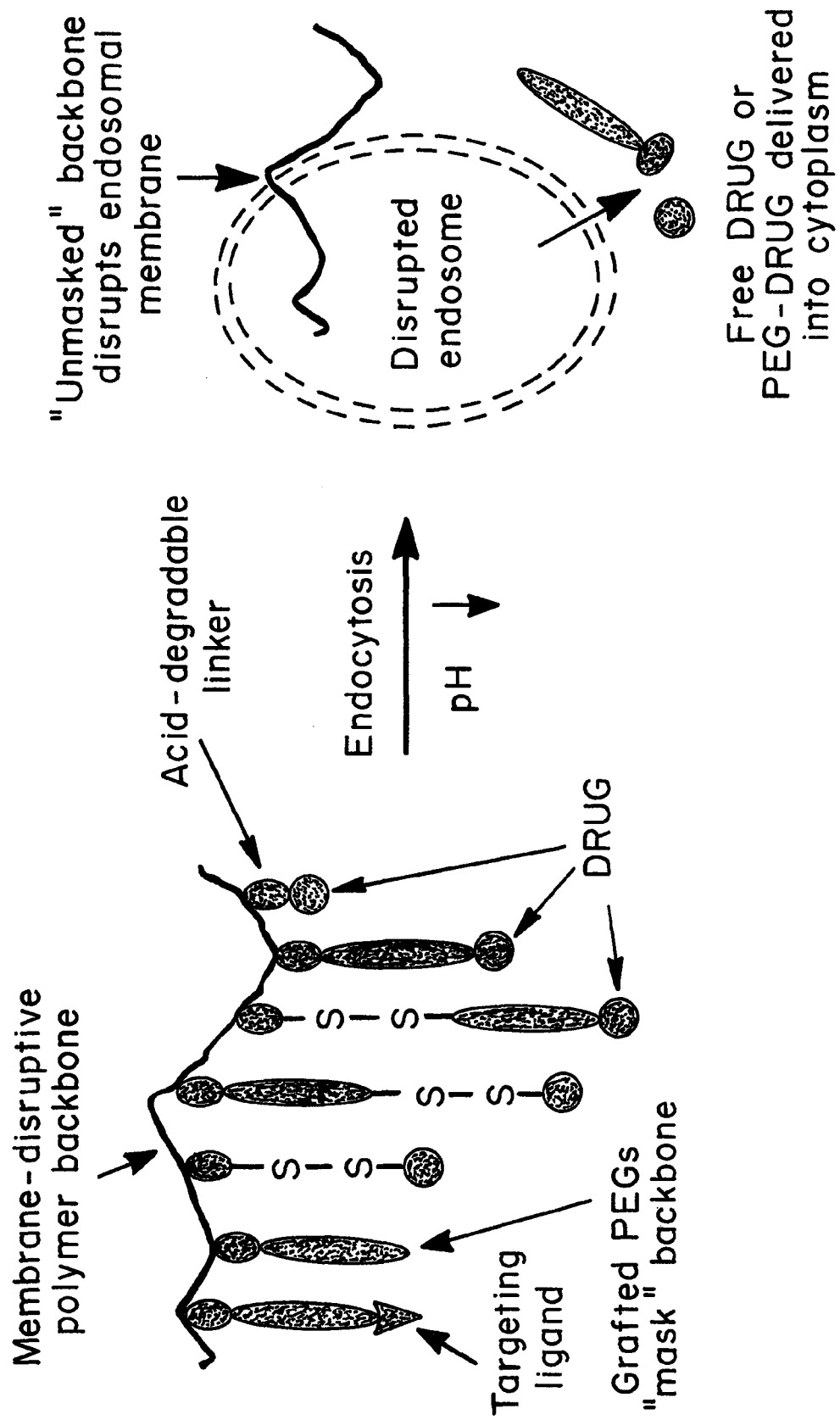
FIG. 3 is a schematic of three polymer conjugates. The drug is connected to the membrane disruptive polymer backbone in a number of different manners, including directly, via PEG groups, via disulfide linkages, or via PEG-disulfide groups through the use of acid degradable linkages. This figure also depicts how the drug is delivered to the cytoplasm.

A schematic diagram of a composition for enhancing membrane transport of drugs is depicted in FIG. 3. The composition has the following components: a membrane-disruptive backbone (line), acid-degradable linkers (oval), PEG grafts (ellipsoid), conjugated drug molecules (oval) and a conjugated targeting ligand (arrow). At pH 7.4 the polymers are serum stable and nontoxic because they are PEGylated ("masked"); however, after endocytosis the acid-degradable linker hydrolyzes and the polymer backbone becomes de-PEGylated ("umasked") and membrane-disruptive, causing endosomal disruption. In an alternative embodiment, the backbone could contain pH-sensitive groups, such as PPAA, and thus would be soluble at pH 7 so it would not need to be PEGylated and then "unmasked" after lowering the pH.

Other suitable hydrophilic polymers include polyethyleneoxide-polypropyleneoxide block co-polymers, such as the PEO-PPO-PEO block copolymers marketed by BASF as Pluronics™; polyvinyl pyrrolidone; polyacrylamide or methacrylamide and their derivatives, such as N-alkyl amides or hydroxyalkyl amides; polyacrylic or methacrylic acid; poly alkylacrylic acids, such as poly(propyl acrylic acid); poly HEMA; polyvinyl alcohol; cellulosics, such as hydroxyethyl cellulose (HEC) and carboxymethyl cellulose (CMC); and polysaccharides, such as dextran, hyaluronic acid, alginate, and carrageenan. The hydrophilic polymer may also be a hydrophilic protein or peptide.

b) Groups having an appropriate charge and in an amount neutralizing or "masking" the hydrophobicity of the membrane disruptive component which are coupled directly to the membrane disruptive component Representative groups that can be linked to the hydrophobic polymer to create a "hydrophilic mask" include hydroxyacids such as glycolides, amines, thiols, molecules containing carboxyl group, amino acids, and other small molecules including these groups.

c) Hydrophilic Agents to be Delivered

Although described in more detail, in one embodiment the hydrophobic polymer can be made to appear hydrophilic until after endocytosis by coupling a hydrophilic therapeutic, diagnostic or prophylactic agent, such as most proteins, to the hydrophobic membrane disruptive polymer. By coupling the agent to the hydrophobic polymer using an acid labile linkage, the agent is released and the membranes disrupted at the same time.

III. Degradable or Stimulus Disruptive Linkages Between Hydrophobic Component and Hydrophilic Component and/or Between Hydrophobic Component and a Therapeutic, Diagnostic or Prophylactic Agent.

a) Degradable Linkages

As discussed above, the linkage coupling the hydrophobic membrane disruptive agent to a hydrophilic polymer, agent to be delivered, or hydrophilic groups is critical to obtaining release of the hydrophilic agents and disruption of the cell or organelle membranes. In the preferred embodiment, these are acid labile, cleaving at the pH of the endosome but stable at physiological pH (in the range of 7.0 to 7.8).

The hydrolysis kinetics of the acid degradable linker is critical for delivery of agents systemically. The conjugate must remain linked together during circulation at pH 7.4, but then the linkages should be rapidly degraded at pH 5.0. Endocytosed macromolecules are typically trafficked to lysosomes within 30-60 minutes after endocytosis. Therefore the linkage between a hydrophilic group and the membrane disruptive component should hydrolyze within 30-60 minutes at pHs between 5.0-5.5.

Preferred acid degradable linkages include acetals, orthoesters, cis-aconityl groups, carboxylic acid hydrazones, phosphamides, esters, Schiff bases, vinyl ethers, dithioacetals, tert butyl esters, and carbamates. Additional acid degradable linkages include urethanes, anhydrides, polysaccharides, amides, esters, ethers, thioureas, ureas, thioesters, sulfonamides, phosphoroamidates, and amine N-oxides. See Felix Kratz et al., *Critical Reviews in Therapeutic Drug Carrier Systems*, 16(3):245 (1999) for a comprehensive list of references discussing acid degradable linkages.

In a preferred embodiment, the acid degradable linkages are acetal linkages. The hydrolysis rates of acetals are proportional to the hydronium ion concentration, which increases 250 fold as pH drops from 7.4 to 5.0. R. W. Taft, M. M. Kreevoy, *J. Am. Chem. Soc*, 77:5590 (1955). Therefore, acetals should hydrolyze 250 times faster at pH 5.0 than at pH 7.4. For example, the kinetics of the release of PEG grafts from the Polymer E1 are shown in FIG. 6A. The rate is strongly pH-dependent as expected, with a half-life of 15 minutes at pH 5.4. In contrast, at pH 7.4, less than 10% of the PEG grafts are hydrolyzed after 75 minutes and only 38% are hydrolyzed after 12 hours. The hydrolysis kinetics of the PEG grafts are thus accelerated by a factor of 100 from pH 7.4 to pH 5.4. This is in agreement with the theoretical value for acetal hydrolysis based on the 100 fold increase in the hydronium ion concentration.

For acetal linkages with a compound containing a benzene ring, the rate constant for hydrolysis can be manipulated over a wide range of timescales by changing the substituent group in the para position of the benzene ring, in order to either stabilize or destabilize the carbocation intermediate formed during hydrolysis. T. H. Fife, L. K. Jao, *J. Am. Chem. Soc*, 30:1492 (1965). For example, by changing the para substituent to a methoxy group in Polymer E1 (see FIG. 4), the rate constant for hydrolysis is decreased by a factor of 60. The Hammet_ value for acetal hydrolysis is between −2.8 and −3.2, reflecting the high sensitivity of acetal hydrolysis to substituent groups. E. H. Cordes, H. G. Bull, *Chem Rev*, 5:581 (1974).

Acetal linkages with hydrophobic groups (or with hydrophilic polymers) which also contain other reactive groups for conjugations to the polymer backbone (or to PEG), such as alkyl halides, tosylates, thiopyridals, amines and alcohols can also be made.

Drug molecules and targeting agents may be conjugated by acid-degradable linkages directly to the backbone or at the free ends of the PEGs (see FIG. 3).

An important vinyl comonomer for any of the vinyl type copolymers in section I (A), above, is the acid degradable "hydrophilic" monomer that becomes hydrophobic when the acid degradable bond is broken at the pH in the endosome and the attached hydrophilic polymer is released. Instead of copolymerizing such a monomer with the other monomers listed in section I (A), one could directly conjugate a reactive Z-hydrophobic-X-hydrophilic group or Z-hydrophilic group to hydrophobic polymer backbones with reactive groups as listed in section I (B), where Z is a group that can react with or be activated to react with the reactive groups in the backbone, and X is a pH-degradable linkage.

b) Other Types of Cleavable Linkages

Other physical stimuli can be used to cleave the linkages coupling the hydrophobic and hydrophilic components, such as application of ultrasound, an electrical field, an electromagnetic field, iontopheresis, electroporation or a combination thereof. Alternatively, other types of stimuli can be used, for example, enzymatic degradation or degradation by exposure to a chemically reactive agent. In some cases it may be desirable to include a combination of acid labile, non-biodegradable and physically disruptible linkages in the conjugates, to achieve different release rates of the various components.

IV. Therapeutic, Diagnostic or Prophylactic Agents

Any therapeutic agent, prophylactic agent or diagnostic agent can be ionically or covalently linked, directly or indirectly, to an endosomal membrane disrupting agent, so long as the linkage does not interfere with the activity of the therapeutic, diagnostic or prophylactic agent following administration to the cell and endocytosis. The agent can be directly coupled to the hydrophobic membrane disrupting component or the hydrophilic component, indirectly coupled, via another compound which is coupled to the membrane disrupting agent, such as an endocytosis enhancing agent, a targeting compound, a compound decreasing lysosome function, or a ligand attached to the membrane disrupting agent, such as a polycationic polymer which binds nucleic acid. The therapeutic, diagnostic or prophylactic agent can be coupled to the membrane disruptive agent via a stimulus sensitive linkage, i.e., an ester or acetal bond, which is disrupted upon exposure to a stimulus, for example, a change in pH.

For therapeutic, diagnostic or prophylactic agents that do not contain hydroxyls, the acetal bonds can be derivatized with functional groups that react with thiols and amines, such as thiopyridal groups and N-hydroxy succinimide (NHS) esters. Therapeutic, diagnostic or prophylactic agents can be conjugated directly to aldehyde groups in the backbone, or to the distal ends of the hydrophilic polymer grafts, which are conjugated via acetal groups to the backbone (see FIG. 3). In some cases, disulfide groups can be incorporated in the pendant agent linkages, releasing an agent-S—S—R construct, which regenerates the agent-SH in the reducing environment of the cytosol (see FIG. 3). The composition can also complex ionic agents if it is conjugated with ionic groups of opposite charge to the agent. Like toxins and viruses, the membrane disruptive component of the polymers is masked until the composition reaches the low pH environment of the endosome.

A number of non-vinyl "naturally-derived" or synthesized cationic polymers may be used as the backbone polymer, including synthetic or natural polypeptides such as poly(L-lysine), polyarginine, protamine, chitosan, aminoethyl dextran, and polyethylene imine, as discussed above. These are particular useful for complexing agents such as nucleotide molecules, including oligonucleotides such as antisense (ODNs), ribozymes, and ribozyme guide sequences, as well as genes. Agents to be delivered can be complexed with them (e.g. DNA or ODNs) or conjugated to them. These polymeric backbones can also be modified by conjugating a reactive Z-hydrophobic-X-hydrophilic group or Z-hydrophobic group to their backbones, where Z is a group that can react with or be activated to react with the amine groups in the backbone, and X is a pH-degradable linkage.

The therapeutic and diagnostic agents can be nucleosides, nucleotides or oligonucleotides, proteins or peptides, polysaccharides and other sugars, synthetic inorganic and organic compounds, metals or radioactive compounds or molecules.

Nucleosides, nucleotides, and oligonucleotides include oligomers or polymers of naturally occurring or modified nucleotides, including naturally occurring or modified purine and pyrimidine bases, 2' and 3' modifications such as O-alkyl, halo and azide modifications, and modifications of the phosphate linkages, for example, substitution of phosphorothioate linkages for phosphate linkages. Oligonucleotides include RNA and single and double stranded DNA nucleic acid sequences. The agents can be antisense molecules which bind to complementary DNA (or complementary messenger RNA) to inhibit transcription, genes, aptamers, triplex helix-forming compounds, ribozymes and external guide sequences for ribozymes, DNAzymes, DNA plasmids, and viral vectors. Many plasmids and viral vectors are commercially available and a number have been used in clinical trials, especially adenoviral vectors, retroviral vectors, and adeno-associated viral vectors. Vectors will usually incorporate the gene to be delivered in phase and under the control of appropriate regulatory agents for expression in the cell where the material is to be delivered. Genes may be marker genes, genes encoding defective or missing proteins, or genes encoding a lethal protein.

Preferred compounds for killing cells include glycoprotein-based toxins such as ricin, the B-chain of the diptheria toxin, and peptides derived from adenovirus, influenza virus, and the GAL4 peptide. A representative toxin is ricin. Ricin is a naturally occurring glycoprotein heterodimer that includes an A-chain with N-glycosidase activity capable of inactivating 60S eukaryotic ribosome subunits, and a B-chain capable of binding to cell surface molecules (e.g., galactose residues for ricin B). The A-chain must be delivered to the cytosolic ribosomes for the cells to be killed. Since these toxins bind to virtually every cell via the B-chain, they lack the specificity required to be effective chemotherapeutic agents. Other toxins ribosylate and thereby inactivate elongation factor 2 which is required for protein synthesis. Other representative toxins are abrin, modeccin, *Pseudomonas* exotoxin, bryodin, mistletoe lectin, Shiga toxin, *Escherichia coli* labile toxin, Pertussis toxin, cholera toxin, anthrax toxin, viscumin, saporin, gelonin, momordin, trichosanthin, and pokeweed antiviral protein.

Toxins can be conjugated to an antibody specific for targeted cells. Polysaccharides such as heparin can also be used, where the polysaccharide binds to receptors on the cell surface. Compounds with a wide range of molecular weight, for example, between 100 and 500,000 Daltons can be used.

When the agent to be delivered is a toxin in combination with an antibody targeted to the cells to be killed, the resulting conjugate is an immunotoxin, which can be effectively delivered to the cytosol. The carbohydrate moiety present in the Fc regions of antibodies is a convenient location for conjugation. When oxidized, these carbohydrate regions yield aldehyde groups, which are not present elsewhere on the protein. Since this region lies away from the epitope binding site, it minimizes interference with antigen binding. Additionally, it leaves the lysine residues of the antibody, a readily accessible conjugation site, available for subsequent conjugations. The A-chain of toxins, such as Ricin, can be covalently linked to an antibody using known coupling chemistry, for example, using the heterobifunctional cross-linker N-succinimidyl-3-(2-pyridyl-dithio-propionate) (SPDP), or by reductive amination.

Any of a variety of diagnostic agents can be employed. These can be administered alone or coupled to one or more therapeutic agents as described above. The agents can be radiolabeled, fluorescently labeled, enzymatically labeled and/or include dyes or magnetic compounds and other materials that can be detected using x-rays, ultrasound, magnetic resonance imaging ("MRI"), positron emission tomography (PET), computer assisted tomograph ("CAT"), single photon emission computerized tomography, fluoroscopy or other commonly used diagnostic technology. Examples of suitable materials for use as contrast agents in MRI include the gadolinium chelates currently available, such as diethylene triamine pentacetic acid (DTPA) and gadopentotate dimeglumine, as well as chelates of iron, magnesium, manganese, copper and chromium. Examples of materials useful for CAT and x-rays include iodine based materials, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte. Useful ultrasound contrast agents that can be coupled to the membrane disruptive agent include an acoustic contrast agent that is preferentially bright when imaged with diagnostic ultrasound.

Radioactive compounds can also be used therapeutically. Radioisotopes include indium ("In"), iodine ("131I"), and yttrium ("90Y") isotopes, which can be cytotoxic.

These materials can be coupled to the conjugate using standard chemical techniques, or in some cases, using recombinant technology, for example, to make a fusion protein. Wilder et al., *J. Clin. Oncol.* 14:1383-1400 (1996). Covalent linkages can be formed using chemical reactions well known to those of skill in the art. For example, glycoproteins often have saccharide moieties, which can be oxidized to provide aldehyde groups. Aldehyde groups are known to react with amines to form Schiff bases, which can then be reduced with sodium cyanoborohydride in a process known as reductive amination. Peptides which have amine groups and carboxylic acid groups, polymers with carboxylic acid groups, and polymers and peptides with imidazole groups and other groups which hydrolyze phospholipid membranes at the pH range within the endosomes can be covalently coupled using methods well known to those of skill in the art. The agent can be coupled via a degradable linkage, such as an acetal, anhydride, ester, orthoester, amide, Schiff base or disulfide linkage, or a stimuli disruptible linkage, as discussed above in section IIIb. In the preferred embodiment, these linkages are acid degradable, as discussed in the foregoing section IIIa.

Agents can be coupled ionically to a complex forming material, which is covalently coupled to the endosomal membrane disrupting agent. Oligonucleotides and other negatively charged materials, such as anthracycline antitumor agents, are known to form complexes with polycationic materials. Suitable polycationic materials include synthetic and natural polyamines, such as chitosan, poly(ethyleneimine) (PEI), poly(N,N-dimethylaminoethyl methacrylate) (PDMAEMA), polyamidoamine (PAMAM), poly(vinyl pyridine), poly(vinyl imadazole), poly(vinyl amine) (obtained by hydrolysis of polyvinyl formamide), quaternized forms of these amines, and starburst dendrimers with cationic functional groups which are positively charged at lower pH. Polycationic materials can be covalently or ionically linked to the endosome disrupting agents and ionically complexed to negatively charged agents to be delivered. The complex may both stabilize and enhance endocytosis. Intercalating compounds can also be used for delivery of nucleic acids. For example, PEAA can be covalently linked to ethidium bromide. Other intercalating agents include some of the porphyrins and phthalocyanines.

V. Endocytosis Enhancing Agents and Targeting Agents

Endocytosis enhancing agents can be ionically or covalently coupled, directly or indirectly, to the conjugate. Exemplary endocytosis enhancing agents include antibodies and membrane-receptor ligands such as transferrin, which non-specifically bind the endosomal membrane disrupting agent to the cell where the agent is to be delivered; polycations; and phospholipases. Other ligands that interact with receptors on the cell surface include transferrin, galactose, asialoorosomucoid, insulin, cytokines, such as interleukin 2, and growth factors, such as epidermal growth factor, platelet derived growth factor and nerve growth factor. Examples of conjugates of endosomal membrane disrupting agents and endocytosis enhancing agents include poly(ethylacrylic acid) (PEAA) directly conjugated to IgG and steptavidin conjugated to a ligand (e.g., IgG), then complexed with biotinylated PEAA (B-PEAA), to indirectly conjugate the endosomal membrane disrupting agent with the endocytosis enhancing agent.

Other compounds that appear to enhance endocytosis and/or membrane disruption may also be included in the formulation. Polycations, such as polylysine, are particularly effective when used in combination with negatively charged materials, such as oligonucleotides. In another embodiment, the endosomal membrane disrupting agent is ionically or covalently conjugated, directly or indirectly, with enzymes such as phospholipases, neuroamidases and sphingomylinases, which are capable of hydrolyzing lipids, thereby further enhancing membrane disruption. Suitable enzymes include the sphingomylinase isolated from the human placenta and phospholipase A2 from lysosomes. Other compounds which are not directly linked to the membrane disrupting agent or endocytosis enhancing agent but which are known to have these properties, such as glycerol, may also be included in the formulations.

Examples of molecules found on the surface of specific cell types include cell type specific antigens (which can be specific to species, individual, or tissue of origin), viral antigens (in the case of virally infected cells), and tumor antigens. These molecules can be targeted using antibodies, preferably monoclonal antibodies, most preferably human monoclonal antibodies or humanized antibodies, or using receptor-specific ligands. Tumor antigens are useful as targets for antibody-conjugated chemotherapeutic or cytotoxic agents. These are not specific markers for tumor cells in most cases; rather, they are over-expressed on tumor cells compared with normal tissue, or they are found in association with normal fetal tissue, such as CEA (Gold, et al., *J. Exp. Med.*, 122:467-481 (1965)), AFP (Abelev, *Adv. Cancer Res.*, 14:295-350 (1971) or with normal progenitor cells of that organ in the adult (CEA). Tumor antigens can be localized in the tumor interstitium, on the tumor cell membrane, or in the tumor cell cytoplasm or nucleus.

Antigens that are found on cells in circulation and antigens expressed on tumor neovasculature are readily accessible to intravenous (i.v.) administered reagents. Antigens that are expressed on the surface of tissue or tumor cells are readily accessible to intralesional (i.l.) or intraperitoneal (i.p.) administered conjugates. Antigens secreted into the tumor interstitium are most accessible to i.l. administration.

The membrane disruption agents can be conjugated to cell ligands via spacer arms, such as polyethylene glycol (PEG). This could enhance the effectiveness of the endosomal membrane disruption agent (it really enhances the effectiveness of the cell ligands). The effectiveness of disruption agents grafted to disruption polymer backbones (e.g., GAL4-g-PAA) is improved by conjugating or grafting them to the polymer via PEG spacer arms.

VI. Compounds which Minimize Lysosome Function

The formulations including membrane disruptive agents for disruption of endosomes can also include effective amounts of compounds which minimize lysosome function. Any compound which minimizes lysosome function without interfering with the efficacy of the agent to be delivered or the endosome disrupting agent can be used. Examples include lysosomal enzyme inhibitors in general. Other suitable compounds include amantadine, verapamil, chloroquine, chlorpromazine, monensin, and ammonium chloride.

VII. Carriers

The compositions described herein can be incorporated into nano- and microparticles, including microspheres and microcapsules, liposomes, lipid vesicles, emulsions or polycationic complexes, using any method that does not destroy the activity of the agents to be delivered. The compositions can be in solution, applied to solid surfaces or formed into hydrogels. The solid surfaces should allow for the compositions to come in contact with systems containing cells. Suitable surfaces include nanoparticles, microparticles, membranes, porous solids, and cell culture surfaces. The polymers can be immobilized on the surfaces by covalent bonds (e.g., chemically grafted to the surface) or by physical interactions (e.g., via ionic, polar, and/or hydrophobic interactions). Additionally, the compositions could be formed into crosslinked hydrogels. Further, the hydrogels could be applied to the solid surfaces described above. The solutions, coated particles or hydrogels could be used as drug-carriers. In a preferred embodiment, the compositions are drug-carriers in the form of nanoparticles.

In other embodiments, the disrupting agents are coupled by ionic, covalent or hydrophobic coupling of the polymers with cationic lipids or the particulate carriers. In a preferred embodiment, the endosomal membrane disrupting agent is a polymer which is hydrophobic (at acidic pHs) or has been hydrophobically modified, for example by conjugation with cholesterol which can be incorporated into a liposome, especially cationic liposomes, so that the polymer is actually a part of the delivery system. These liposomes can be used alone with the membrane disrupting agent or in combination with the membrane disrupting agent and an enhancer such as ultrasound, electric field, and/or stimuli.

Microparticles and nanoparticles may be prepared using single and double emulsion solvent evaporation, spray drying, solvent extraction, solvent evaporation, phase separation, simple and complex coacervation, interfacial polymerization, and other methods well known to those of ordinary skill in the art. Methods developed for making microspheres for drug delivery are described in the literature, for example, as described in M. Doubrow, Ed., "Microcapsules and Nanoparticles in Medicine and Pharmacy," CRC Press, Boca Raton, 1992.

The compositions can also be administered in other physiologically acceptable vehicles, such as phosphate buffered saline, or other vehicles for topical, local, interstitial or intravenous administration.

B. Methods of Administration

I. Delivery of Therapeutic, Diagnostic or Prophylactic Agents

The compositions can be administered to cells directly, topically, in suspension, as an ointment or spray, or to an animal, systemically, regionally (intralesionally) or locally. The cells may be any type of cell in the body, including blood cells, tissue cells, and mucosal cells. An effective dosage can be determined by an alteration in cell activity—for example, by measuring cell death, by detection of a diagnostic agent, or by measuring transport of a particular analyte. The compositions can be administered in a single bolus, continuously, or repeatedly.

In a preferred embodiment, the compositions are administered in vitro to the cells. For example, stem cells are removed from the body, treated with the compositions, alone or in combination with an enhancer such as ultrasound, in vitro to introduce genetic material into the cells, then reintroduced into the patient to be treated. In another example, bacterial cells are treated with the compositions and a stimulus is applied to cause membrane disruption. The stimulus can be a change in pH.

As described in the examples, a test which is predictive of disruption of endosomal membranes is the erythrocyte hemolysis test. The endosomal membrane disruptive properties are evaluated by determining the extent of lysis of erythrocytes. The hemolysis assay involves adding a small volume (e.g., 500 micrograms or 0.5 g of composition in a 1% solution, about 0.005 ml) solution of the composition to a red blood cell suspension of approximately 108 cells (in about 1 ml), and incubating for one hour at 37_C. After incubation, the cells are centrifuged, and the absorbance of the supernatant is measured at 541 nm. This reflects the number of lysed cells.

If further studies are desired, one can label the compositions with a pH-dependent fluorophore as discussed in M. J. Geisow, "Fluorescein Conjugates as Indicators of Subcellular pH", *Experimental Cell Research*, 150:29-35 (1984). The endocytosis of the conjugates by cells, and their trafficking, is followed via visualization of the fluorophore. Depending on the emission maximum, one can determine whether the composition is in an environment of low pH (the endosome) or of physiological pH (the cytoplasm).

In those embodiments including an endocytosis enhancing agent, these experiments can determine whether the agent's affinity has been altered by conjugation, as well as whether the membrane disruptive capabilities of the polymer are effective in stimulating endosomal release.

II. For Extraction of Cellular Contents

Although described primarily herein with reference to transport of agents into cells, the same technology can also be used to enhance transport out of cells or through cell layers. Any type of cell in the body, such as blood cells, tissue cells and mucosal cells, or cellular organelles, or microorganisms such as bacterial cells, can be made permeable by acidifying a mixture of the cells and the membrane disruptive polymer (plus any useful chemical agents) to recover and assay analytes, cell or organelle components, infective agents (bacterial, parasitic, or viral), genetic material, or even previously administered therapeutic or diagnostic compounds. After the cells are made permeable, a variety of separation steps and chemistries may be run on the extracted materials to recover or assay selected compounds. The end point of the assay may result in a visual color change, or a quantitative measure of a metabolite of interest. Additionally to the pH change, one can enhance the transport of metabolites or other analytes in interstitial fluid or within the cytosol or across membrane barriers by administration of the disrupting agents and administration of an appropriate stimulus or stimuli such as light, ultrasound, electric field or change in temperature.

The compositions and methods described herein will be better understood with reference to the following non-limiting examples.

Example 1 pH mediated Disruption of Membranes using Acetal-PEG-Copolymer

This example demonstrates that an acetal-PEG-copolymer can act as an endosomal releasing agent. This was determined by measuring the hemolytic activity of the above polymers at endosomal pH (5.5) and physiologic pH (7.4).

Synthesis of the polymeric conjugate is shown in FIG. 1.

Hemolysis Assay: Fresh human blood was isolated in EDTA containing vacutainers, washed three times with 150 mM NaCl, and resuspended at a concentration of 108 red blood cells/ml in PBS buffer (2% in 1 ml PBS) at either pH 5.5 or pH 7.4. The polymer was dissolved pH 10 buffered PBS. The appropriate volume of polymer solution was then added to the RBC solution and incubated for 20 minutes at 37° C. The cells were then centrifuged and the degree of hemolysis was determined by measuring absorbance of the supernatant at 541 nM. A 100% lysis was determined by lysing the red blood cells in deionized water. The controls were RBCs suspended in buffer without polymer. Experiments were done in triplicate with a standard deviation of less than 2%.

Figure 2:
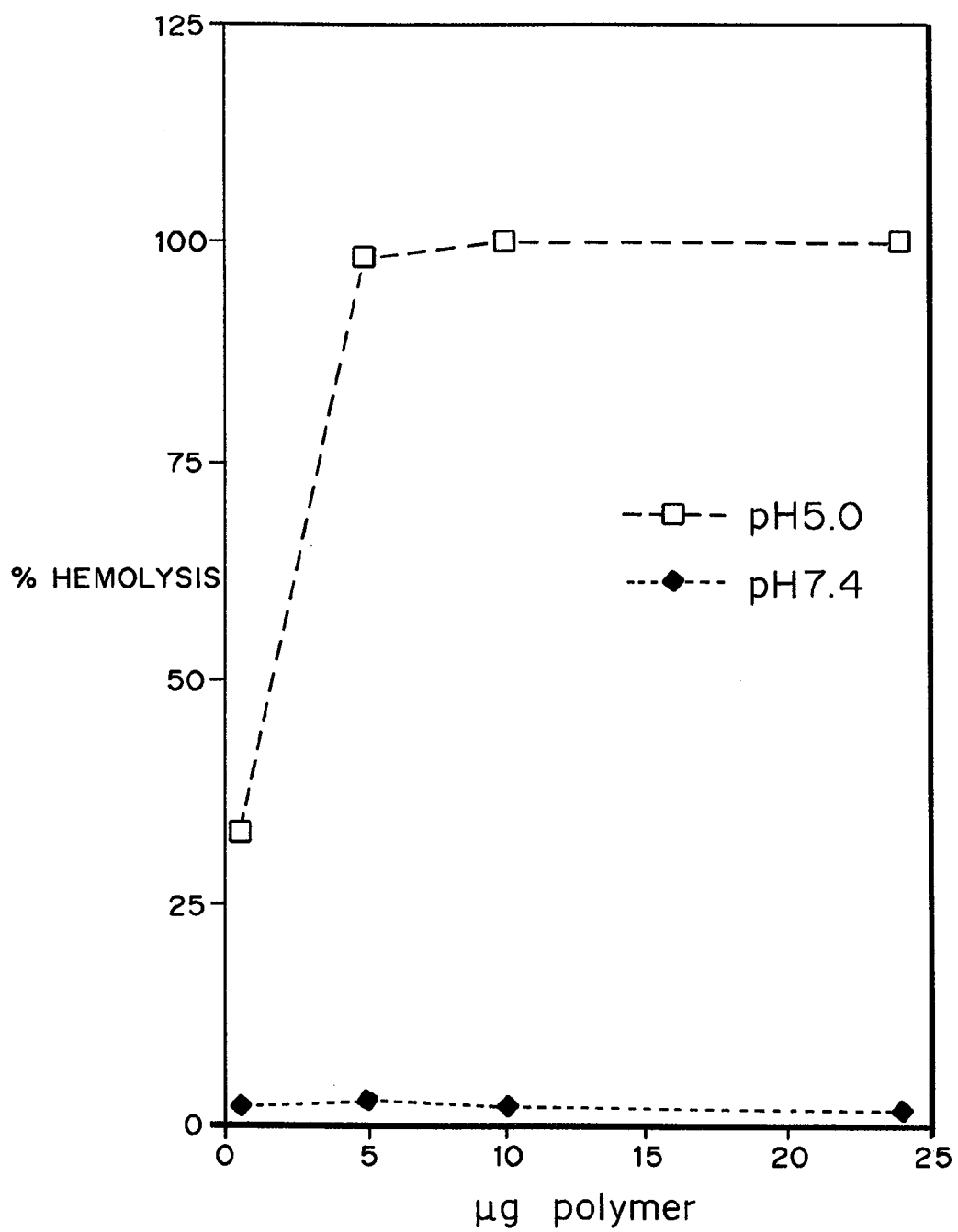
FIG. 2 is a graph of the percent hemolysis by the conjugate of FIG. 1 at pH 5.0 (squares) compared to lysis at pH 7.4 (diamonds) as a function of the amount of polymer (micrograms).

The results of the hemolysis assay are shown in FIG. 2. The polymer caused 100% lysis at the lowest concentration tested, five micrograms of polymer at pH 5.0 and unmeasurable lysis at pH 7.4.

Example 2

Figure 4:
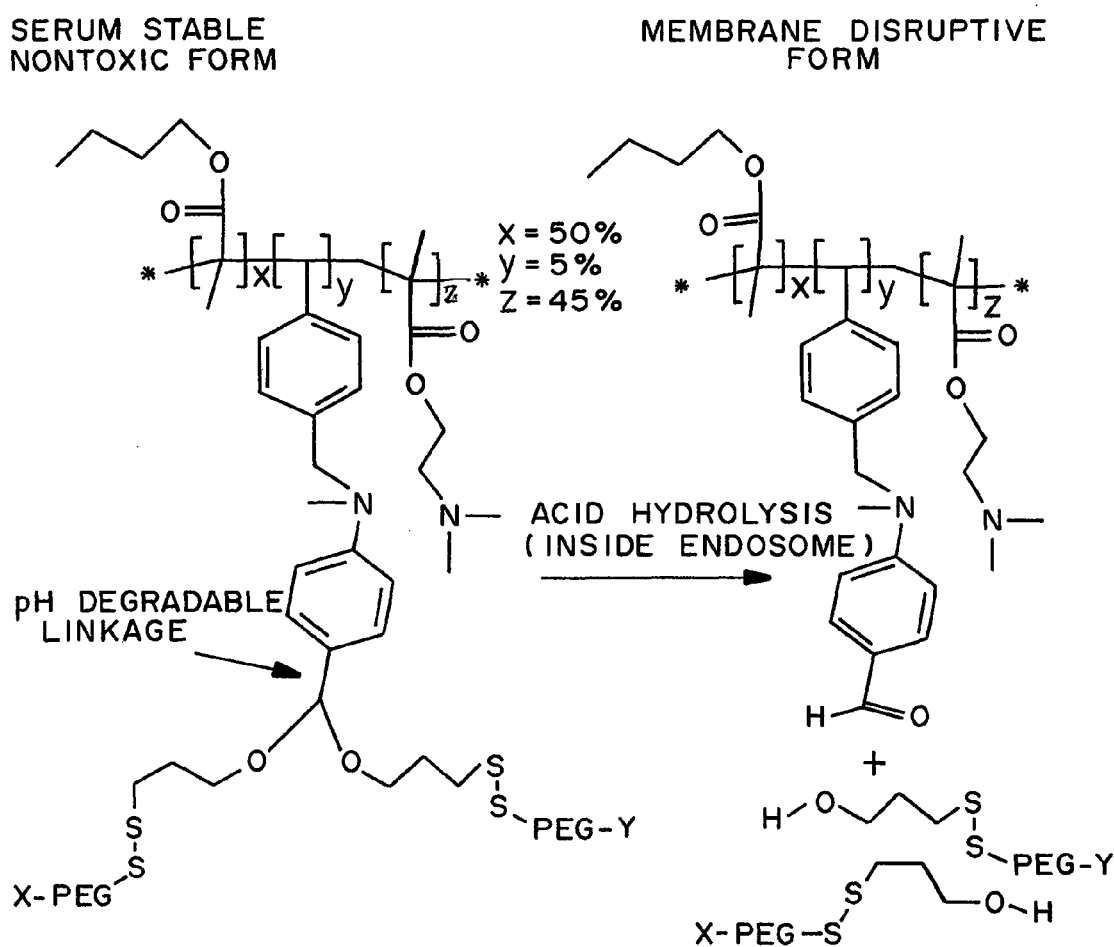
FIG. 4 shows the chemical structure of three embodiments of the described compositions, Polymer E1, Polymer E2 and Polymer E3. In each of these compositions, the membrane-disruptive backbone is a terpolymer of butyl methacrylate (BMA), dimethylaminoethyl methacrylate (DMAEMA) and styrene benzaldehyde.

Synthesis of Compositions Containing a Terpolymer of Dimethylaminoethyl Methacrylate, Butyl Methacrylate and Styrene Benzaldehyde for pH Mediated Disruption of Membranes A terpolymer of dimethylaminoethyl methacrylate (DMAEMA), butyl methacrylate (BMA) and styrene benzaldehyde was chosen for the membrane-disruptive backbone (see FIG. 4). Copolymers of BMA and DMAEMA are extremely effective membrane disruptive agents, a property that can be attributed to their cationic and hydrophobic components, leading to a surfactant-like character. C. Hansch, W. R. Glave, *Mol. Pharmacol,* 7:337 (1972).

Figure 5A:
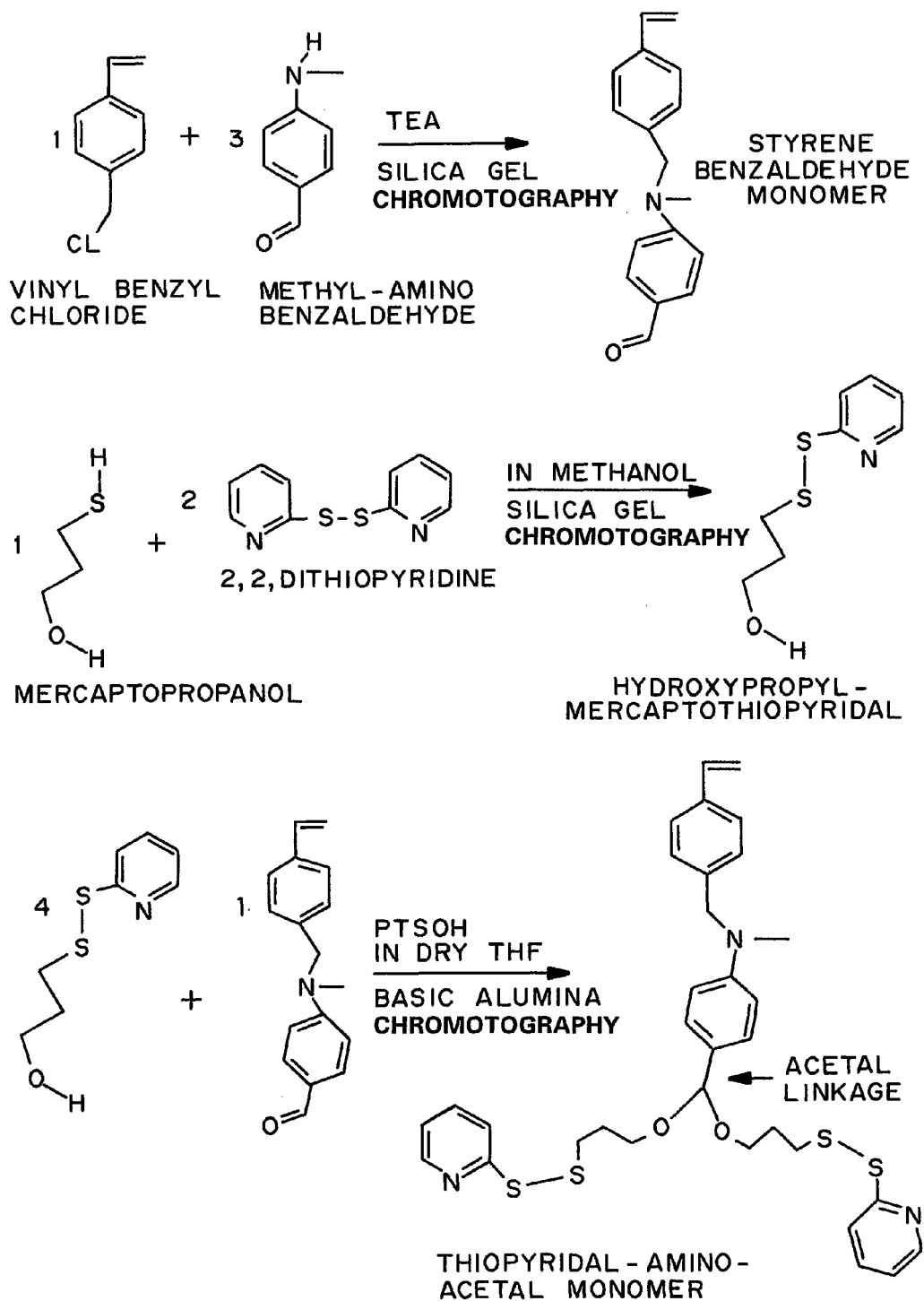
FIGS. 5A and 5B are a schematic of the synthesis of the composition depicted in FIG. 4.
Figure 5B:
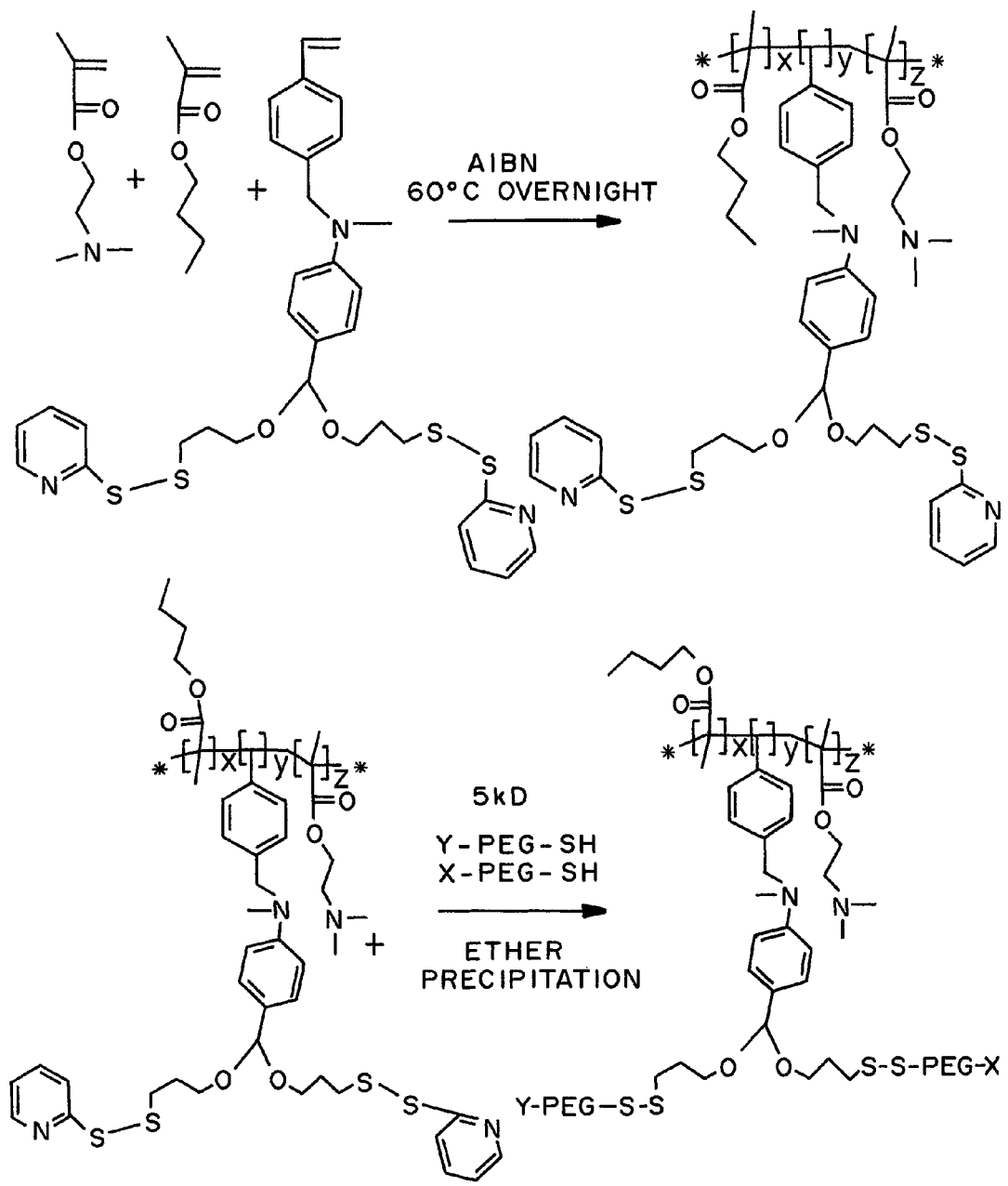

The strategy used to synthesize the compositions is depicted in FIGS. 5A and 5B. The first step was the synthesis of a functionalized acetal monomer. This monomer was then copolymerized with DMAEMA and BMA using a free radical polymerization process. The resulting terpolymer was purified by precipitation in hexane and then PEGylated with thiol-terminated monofunctional or heterobifunctional PEGs. The PEGylated polymers were purified by ether precipitation. The acid-degradable linkage is a para-amino benzaldehyde acetal. The PEG grafts have a molecular weight of 5kD. Three different compositions were formed from the PEGylated terpolymer; Polymer E1, in which the PEG grafts are terminated with a methoxy group, Polymer E2, in which the PEG grafts are terminated with lactose or, fluorescein-isothiocynate (FITC), and Polymer E3, in which the PEG grafts are terminated with lactose or hexylysine. The chemistry described herein to conjugate drug molecules can be easily modified to incorporate a variety of other conjugation strategies (see FIG. 3 for examples).

Example 3

Hydrolysis and Hemolysis Studies with Polymer E1

The hydrolysis of polymer E1 was measured at 37° C., in phosphate buffer, at either pH 5.4 or 7.4, by observing the change in U.V. absorbance at 340 nm. The experiments were done in triplicate and the standard deviation was under 5% for all samples.

The ability of polymer E1 to stimulate pH-induced membrane disruption was tested by assaying its ability to disrupt red blood cell membranes (RBCs) at pH 5.0 and pH 7.4 (FIG. 6B). One-hundred million RBCs in a 1 ml volume of phosphate buffer were used in each experiment. The incubation time was 20 minutes at 37° C. The experiments were done in triplicate and the standard deviation was under 5% for all samples. The protocol used to isolate and purify the red blood cells and quantitate hemolysis is described in N. Murthy, J. R. Robichaud, D. A. Tirrell, P. S. Stayton, A. S. Hoffman, *J. Contr Rel,* 61:137 (1999).

Only 0.5-5 µg/ml of the polymer E1 was required for efficient hemolysis of 108 RBCs at pH 5.0 after 20 minutes, whereas at pH 7.4 only background levels of hemolysis were observed after 20 minutes for polymer concentrations up to 25 µg/ml (see FIG. 6B). Importantly, the membrane-disruptive activity of this polymer occurs within 20 minutes upon acidification to pH 5.0. Because vesicular transport in hepatocytes from endosomes to lysosomes has been estimated to take approximately 45 minutes, the kinetics of membrane disruption were appropriate for further biological studies.

Example 4

Study of the Role of PEG Groups in the Membrane Disrupting Activity using Modified Polymer E1

Modified Polymer E1 was synthesized where the acetal-containing monomer was modified to contain a methoxy substituent at the para position of the benzene. This modification extends the hydrolysis half-life of the PEG grafts to 14 hours at pH 5.0.

Modified Polymer E1 did not disrupt red blood cell membranes at pH 5.0 after a 30 minute incubation period, at concentrations between 1-100 µg/ml. Further, less than 5% of the polymer's PEG grafts were hydrolyzed during this time period. After hydrolyzing the PEG grafts of this polymer by incubating it at pH 3.0 for one hour, the free membrane-disruptive backbone caused 100% hemolysis at pH 5.0, and 5 µg/ml concentration. Thus, these results demonstrate that the hydrolysis of the PEG grafts activates the membrane-disruptive activity of the backbone of the polymer.

Example 5

Study of the Ability of Membrane Disrupting Agents to Enhance Cytoplasmic Delivery of Macromolecules into Mammalian Cells using Polymer E2

The ability of the membrane disrupting agent to enhance the cytoplasmic delivery of macromolecules into mammalian cells was investigated in a hepatocyte model system using Polymer E2 (described in Example 2). This system utilized lactose targeting of the asialoglycoprotein (ASGP) receptor, which triggers receptor-mediated endocytosis (RME). B. Tycko et al., *J. Cell. Biol.*, 97:1762 (1983). Internalization via the ASGP receptor has been shown to direct rapid lysosomal accumulation of targeted macromolecules. B. Tycko et al., *J. Cell. Biol.*, 97:1762 (1983).

Polymer E2 was synthesized as described in Example 2 with its PEG grafts terminated with either fluorescein-isothiocynate (FITC) or lactose. This polymer was then incubated with normal mouse hepatocytes (NMH) to determine if Polymer E2 could deliver PEG-FITC (5 kD) (as a model macromolecular drug) into the cytoplasm of living cells. As a control, PEG-FITC (5 kD) alone was incubated with hepatocytes.

A confluent monolayer of normal mouse hepatocytes (NMH cells) was treated with PEG-FITC conjugated to Polymer E2 at a 0.2 mg/ml concentration of PEG-FITC, after a 12 hour incubation. The fluorescently-labeled PEG was spread diffusely throughout the cytoplasm, but not in the nucleus, indicating that the polymer enhanced endosomal release. The PEG-FITC is too large to diffuse into the nucleus, and hence the nuclei appear dark.

A confluent monolayer of NMH cells was treated with PEG-FITC alone at a 0.5 mg/ml concentration, after a 12 hour incubation. The PEG-FITC was able to enter the hepatocytes by fluid phase endocytosis, but unable to escape the endosome.

No toxicity or cell death was seen after 12 to 24 hours of incubation of Polymer E2 with NMH cells.

Example 6

Study of the Ability of Membrane Disrupting Agents to Direct Cytoplasmic Entry of a Biological Macromolecule using Polymer E3

To test whether the polymers could direct cytoplasmic entry of a biological macromolecule, the delivery and trafficking of fluorescently-labeled oligodeoxynucleotides (ODNs) complexed to Polymer E3 were determined by fluorescent microscopy. Polymer E3 was synthesized as described in Example 2 with its PEG grafts terminated with either hexylysine (approximately 20%) or lactose (approximately 80%) for targeting. The polymer was subsequently complexed with rhodamine-labeled ODNs and then incubated with hepatocytes.

NMH cells were treated with rhodamine-labeled oligonucleotides complexed with Polymer E3, at a 30 µg/ml concentration of oligonucleotide and after a 3 hour incubation. The NMH cells displayed a diffuse cytoplasmic/nuclear fluorescence, indicating endosomal/lysosomal disruption. Thus, the rhodamine-labeled ODNs carried by Polymer E3 were rapidly released into both the cytoplasm and nucleus of hepatocytes.

NMH cells were treated with rhodamine-labeled oligonucleotides at a 30 µg/ml concentration after a 3 hour incubation. The NMH cells displayed a punctate fluorescence, indicating that the rhodamine-labeled oligonucleotides were sequestered in lysosomes.

The presence of the rhodamine-labeled ODNs in the nucleus of the hepatocytes suggests that the ODNs disassociated from Polymer E3 because the complex of the ODN and Polymer E3 would be too large to enter the nuclear pores. For example, in Example 5, PEG-FITC by itself was too large to enter the nuclear pores of hepatocytes. The addition of the terpolymer construct enhances the cytoplasmic entry of ODNs. Thus, these compositions can provide a direct route to enhancing antisense ODN therapeutic delivery.

The teachings of the references cited herein are specifically incorporated herein. Modifications and variations of the present invention will be obvious to those skilled in the art from the foregoing detailed description and are intended to be encompassed by the following claims.

We claim:

1. A method for disrupting a cell or organelle membrane comprising delivering to the cell or organelle a composition comprising a water-soluble hydrophilic conjugate having a hydrophobic component linked to a hydrophilic component by a pH-sensitive linkage,
   wherein the pH-sensitive linkage is stable at a pH between 6.8 and 8 and hydrolyzed at a pH less than 6.5 to release the hydrophobic component;
   wherein the hydrophilic component comprises a polyalkylene oxide;
   wherein the hydrophobic component is an endosomal membrane disruptive vinyl copolymer prepared from alkyl substituted methacrylates, cationic monomers, and polyethylene glycol amino acetal monomers that provides transport through the endosomal membrane when released from the hydrophilic conjugate.

2. The method of claim 1 wherein the cell is in a patient a human cell.

3. The method of claim 1 wherein the composition further comprises a therapeutic, prophylactic or diagnostic agent.

4. The method of claim 3, wherein the therapeutic, prophylactic or diagnostic agent is selected from the group consisting of a protein, a peptide, a saccharide, a polysaccharide, an organic molecule, a nucleotide, an antisense nucleotide, an oligonucleotide, a ribozyme, a ribozyme guide sequence, a triplex forming oligonucleotide, and a gene.

5. The method of claim 3, wherein the therapeutic, prophylactic or diagnostic agent is a nucleotide or nucleoside.

6. The method of claim 3, wherein the therapeutic, prophylactic or diagnostic agent is an oligonucleotide.

7. The method of claim 3, wherein the therapeutic, prophylactic or diagnostic agent is an RNA oligonucleotide.

8. The method of claim 1, wherein the vinyl copolymer is a random, block, or graft copolymer.

9. The method of claim 1, wherein the cationic monomer is diethylaminoethyl methacrylate.

10. The method of claim 1, wherein the alkyl-substituted methacylate is butyl methacrylate.

11. The method of claim 9, wherein the copolymer is prepared from monomers further comprising butyl methacrylate or styrene.

12. The method of claim 9, wherein the copolymer further comprises dimethylaminoethyl methacrylate.

13. A method for disrupting a cell or organelle membrane comprising delivering to the cell or organelle a composition
   wherein the composition comprises a hydrophilic conjugate having
   (a) a hydrophobic synthetic vinyl polymer, wherein the polymer is an endosomal membrane disruptive polymer prepared from alkyl substituted methacrylates, cationic monomers, and polyethylene glycol amino acetal monomers that provides transport through an endosomal membrane when released from the hydrophilic conjugate;
   (b) a plurality of pendant hydrophilic polyalkylene oxide components; and
   (c) a plurality of pH-sensitive linkages, wherein each of the pendant polyalkylene oxide components is covalently linked to the polymer through a pH-sensitive linkage that is stable at a pH between 6.8 and 8 and hydrolyzed at a pH less than 6.5.

14. The method of claim 13, wherein the cell is a human cell.

15. The method of claim 13, wherein the composition further comprises a therapeutic, prophylactic or diagnostic agent.

16. The method of claim 15, wherein the therapeutic, prophylactic or diagnostic agent is selected from the group consisting of a protein, a peptide, a saccharide, a polysaccharide, an organic molecule, a nucleotide, an antisense nucleotide, an oligonucleotide, a ribozyme, a ribozyme guide sequence, a triplex forming oligonucleotide, and a gene.

17. The method of claim 15, wherein the therapeutic, prophylactic or diagnostic agent is a nucleotide or nucleoside.

18. The method of claim 15, wherein the therapeutic, prophylactic or diagnostic agent is an oligonucleotide.

19. The method of claim 15, wherein the therapeutic, prophylactic or diagnostic agent is an RNA oligonucleotide.

20. The method of claim 13, wherein the vinyl copolymer is a random, block, or graft copolymer.

21. The method of claim 13, wherein the cationic monomer is diethylaminoethyl methacrylate.

22. The method of claim 21, wherein the alkyl-substituted methacylate is butyl methacrylate.

23. The method of claim 21, wherein the copolymer is prepared from monomers further comprising styrene.

24. The method of claim 21, wherein the copolymer further comprises dimethylaminoethyl methacrylate.

25. A method for disrupting a cell or organelle membrane comprising delivering to the cell or organelle a composition comprising a hydrophobic component linked to a hydrophilic component by a pH-sensitive linkage;

wherein the pH-sensitive linkage is stable at a pH between 6.8 and 8 and hydrolyzed at a pH less than 6.5 to release the hydrophobic component;

wherein the hydrophilic component comprises a polyalkylene oxide;

wherein the hydrophobic component comprises a random, block, or graft copolymer prepared from alkyl substituted methacrylates, cationic monomers, and polyethylene glycol amino acetal monomers;

and wherein the hydrophobic component is an endosomal membrane disruptive copolymer that provides transport through the endosomal membrane when released from the hydrophilic component.

26. The method of claim 25, wherein the cell is a human cell.

27. The method of claim 25, wherein the composition further comprises a therapeutic, prophylactic or diagnostic agent.

28. The method of claim 27, wherein the therapeutic, prophylactic or diagnostic agent is selected from the group consisting of a protein, a peptide, a saccharide, a polysaccharide, an organic molecule, a nucleotide, an antisense nucleotide, an oligonucleotide, a ribozyme, a ribozyme guide sequence, a triplex forming oligonucleotide, and a gene.

29. The method of claim 27, wherein the therapeutic, prophylactic or diagnostic agent is a nucleotide or nucleoside.

30. The method of claim 27, wherein the therapeutic, prophylactic or diagnostic agent is an oligonucleotide.

31. The method of claim 27, wherein the therapeutic, prophylactic or diagnostic agent is an RNA oligonucleotide.

32. The method of claim 25, wherein the alkyl substituted methacrylate is butyl methacrylate.

33. The method of claim 25, wherein the copolymer further comprises dimethylaminoethyl methacrylate.

* * * * *

UNITED STATES PATENT AND TRADEMARK OFFICE
CERTIFICATE OF CORRECTION

PATENT NO.         : 8,318,816 B2
APPLICATION NO.    : 12/771850
DATED              : November 27, 2012
INVENTOR(S)        : A. S. Hoffman et al.

Page 1 of 1

It is certified that error appears in the above-identified patent and that said Letters Patent is hereby corrected as shown below:

In the Claims

| COLUMN | LINE | ERROR |
|---|---|---|
| 24 (Claim 2, | 26 line 1) | delete the phrase "in a patient" |
| 24 (Claim 11, | 49-50 lines 2-3) | delete the phrase "butyl methacrylate or" |

Signed and Sealed this
Fifteenth Day of July, 2014

Michelle K. Lee
*Deputy Director of the United States Patent and Trademark Office*